(12) United States Patent
Seal et al.

(10) Patent No.: US 11,899,028 B2
(45) Date of Patent: Feb. 13, 2024

(54) BUFFER MANAGEMENT AND IDENTIFICATION IN BIOPROCESSING SYSTEM

(71) Applicant: Cytiva US LLC, Marlborough, MA (US)

(72) Inventors: Michael B. Seal, Hampshire (GB); Darren G. Elton, Hampshire (GB); Bojan Isailovic, Portsmouth (GB); Jeremy Rautenbach, West Berkshire (GB)

(73) Assignee: Cytiva US LLC, Marlborough, MA (US)

( * ) Notice: Subject to any disclaimer, the term of this patent is extended or adjusted under 35 U.S.C. 154(b) by 391 days.

(21) Appl. No.: 17/127,178

(22) Filed: Dec. 18, 2020

(65) Prior Publication Data

US 2021/0199679 A1  Jul. 1, 2021

Related U.S. Application Data

(60) Provisional application No. 62/955,933, filed on Dec. 31, 2019.

(51) Int. Cl.
*G01N 35/00* (2006.01)
*G01N 35/10* (2006.01)
(Continued)

(52) U.S. Cl.
CPC ... *G01N 35/00732* (2013.01); *G01N 35/1009* (2013.01); *B01D 15/08* (2013.01); *B01D 65/00* (2013.01); *G01N 2035/1025* (2013.01)

(58) Field of Classification Search
CPC ......... G01N 35/00732; G01N 35/1009; G01N 2035/1025; G01N 30/468; G01N 30/34;
(Continued)

(56) References Cited

U.S. PATENT DOCUMENTS 5,135,485 A   8/1992  Cohen et al.
9,063,101 B2  6/2015  Tanaka et al.
(Continued)

FOREIGN PATENT DOCUMENTS

EP   2366994 A1 *  9/2011  ............. G01N 27/00
EP   3 160 636      4/2021
(Continued)

OTHER PUBLICATIONS

English-language translation of Jun. 29, 2022 Office Action issued in Chinese counterpart patent application No. 202011623536.0.
(Continued)

*Primary Examiner* — Robert R Raevis
(74) *Attorney, Agent, or Firm* — Leydig, Voit & Mayer, Ltd.

(57) ABSTRACT

A buffer management system includes at least one workstation configured to support a supply of concentrated buffer solution and an inline dilution skid having a manifold and at least one workstation to support delivery of diluted (surge) buffers from the inline dilution skid. The latter workstation also serves to supply ready-made (diluted) buffers to a bioprocessing unit. The manifold is in fluid communication with the supply of concentrated buffer solution and is adapted to be placed in fluid communication with a source of water for injection (WFI). The inline dilution skid is configured to variably mix the supply of concentrated buffer solution and the source of WFI to obtain a range of diluted buffer solutions. Processes for automatically identifying the arrangement of buffer solutions in a bioprocessing application use signals from various sensors to identify the fluid connections between components of the system.

12 Claims, 18 Drawing Sheets

(51) Int. Cl.
*B01D 15/08* (2006.01)
*B01D 65/00* (2006.01)

(58) Field of Classification Search
CPC .............. G01N 21/80; G01N 27/4167; G01N 27/4165; G01N 31/221; B01D 15/08; B01D 65/00; C12M 99/00; C12M 23/40; C12M 41/48; C12M 23/28; C12M 41/26; C12M 41/28; C12M 41/44; B01F 23/49; B01F 35/2206
USPC ....... 73/53.01, 61.41, 61.43, 61.61; 324/425, 324/438; 702/22, 30, 31; 422/68.1, 422/82.01, 63, 67
See application file for complete search history.

(56) References Cited

U.S. PATENT DOCUMENTS

| | | | |
|---|---|---|---|
| 9,067,014 | B2 | 6/2015 | Nelson et al. |
| 9,283,521 | B2 | 3/2016 | Schick et al. |
| 9,327,212 | B2 | 5/2016 | Blank et al. |
| 2008/0279038 | A1 | 11/2008 | Bellafiore et al. |
| 2012/0217192 | A1 | 8/2012 | Blank et al. |
| 2013/0161245 | A1 | 6/2013 | Schick |
| 2021/0197142 | A1 | 7/2021 | Seal et al. |
| 2021/0197189 | A1 | 7/2021 | Isailovic et al. |
| 2021/0199484 | A1 | 7/2021 | Seal et al. |

FOREIGN PATENT DOCUMENTS

| | | | |
|---|---|---|---|
| JP | 2007-240430 | 9/2007 | |
| JP | 2009-519440 | 5/2009 | |
| JP | 2013-506128 | 2/2013 | |
| WO | WO 2000/09069 A1 | 2/2000 | |
| WO | WO-2009018467 A2 * | 2/2009 | ....... G01N 33/54366 |
| WO | WO 2015/200269 A1 | 12/2015 | |
| WO | WO 2016/196801 A1 | 12/2016 | |

OTHER PUBLICATIONS

European Patent Office, Extended European Search Report I European Patent Application No. 20216673, 7 pgs. May 25, 2021.
English-language translation of Aug. 16, 2022 Office Action issued in Korean counterpart patent application No. 2020-189589; 3 pgs.
Singapore Patent Office, Written Opinion; Singapore Patent Application No. 10202013222W, 7 pgs. Sep. 27, 2022.
English-language translation of Nov. 30, 2021 Office Action issued in Japanese counterpart patent application No. P2020-215387.

* cited by examiner

BUFFER MANAGEMENT AND IDENTIFICATION IN BIOPROCESSING SYSTEM

CROSS-REFERENCE TO RELATED APPLICATIONS

This patent application claims the benefit of priority to U.S. Provisional Patent Application No. 62/955,933, filed Dec. 31, 2019, and entitled, "Buffer Management and Identification in Bioprocessing System," which is incorporated in its entirety herein by this reference.

BACKGROUND OF THE INVENTION

A buffer management system typically includes a number of biocontainer bags that contain buffer solution for use in a bioprocessing application. Conventional buffer management systems use weigh scales, typically load cells, to determine weights of liquids within the biocontainer bags for liquid level detection, which is transmitted to an automation system. The weight detected by the weigh scale is converted into a calculated volume value using a conversion factor.

In conventional systems, buffer solutions are made at full strength and produced in large quantities for storage in their respective totes. For a typical bioprocessing application, multiple buffer solutions are used with the demand for each buffer solution being variable and on the order of 2000 liters for each buffer in some situations. The totes are then transported from the buffer preparation area to the process suite. As a result, a bioprocessing process operation and its buffer preparation area with the buffer totes can consume a substantial footprint. In addition, specialized moving equipment is sometimes required for the larger totes, with all the inherent risks.

The management of the buffers used for a given bioprocessing application can require a large number of tube connections. Typically, the management and inspection of these buffer connections is performed manually by the user and can present a significant risk of operator error (such as by making the wrong connection(s)), which can lead to process delays and product loss.

There is a continued need in the art to provide additional solutions to enhance the management of buffer solutions used in various bioprocessing applications. It will be appreciated that this background description has been created by the inventors to aid the reader, and is not to be taken as an indication that any of the indicated problems were themselves appreciated in the art. While the described principles can, in some aspects and embodiments, alleviate the problems inherent in other systems, it will be appreciated that the scope of the protected innovation is defined by the attached claims, and not by the ability of any disclosed feature to solve any specific problem noted herein.

BRIEF SUMMARY OF THE INVENTION

The present disclosure, in one aspect, is directed to embodiments of a buffer management system used in a bioprocessing system. In embodiments, the buffer management system can be used to create a plurality of buffer solutions from a corresponding plurality of concentrated buffer solutions for use in a bioprocessing application.

In one embodiment, a buffer management system includes a set of a concentrated buffer solutions, an inline dilution skid, and a control unit. The inline dilution skid includes a single use manifold having a plurality of buffer inlet ports and a buffer characteristic sensor in fluid communication with each one of the buffer inlet ports. The plurality of buffer inlet ports are in respective fluid communication with a different one of the set of concentrated buffer solutions. The buffer characteristic sensor is configured to detect a value of a buffer characteristic of a fluid passing therethrough and to generate a buffer characteristic signal indicative of the sensed value for the buffer characteristic.

The control unit includes a processor, a non-transitory computer readable medium bearing a buffer management program, and a data storage device in operable arrangement with the processor. The processor is in electrical communication with the buffer characteristic sensor to receive the buffer characteristic signal therefrom. The processor is programmed with the buffer management program. The buffer management program has an identification module configured to identify automatically the concentrated buffer solution entering the manifold via one of the buffer inlet ports and passing through the manifold based upon the buffer characteristic signal.

In another aspect, the present disclosure is directed to embodiments of techniques for automatically identifying the arrangement of buffer solutions in a bioprocessing application. In one embodiment, a method of using a buffer management system includes drawing an amount of one of a set of concentrated buffer solutions into a first buffer inlet port of a plurality of buffer inlet ports of a manifold. A buffer characteristic of the concentrated buffer solution is sensed in the manifold. A buffer characteristic signal indicative of a value for the sensed buffer characteristic is transmitted to a control unit. The control unit is used to identify the concentrated buffer solution entering the manifold via the first buffer inlet port based upon the buffer characteristic signal.

In another embodiment, a method of using a buffer management system includes discharging an amount of liquid from a first buffer discharge port of a plurality of buffer discharge ports of a manifold into one of a plurality of biocontainers. The plurality of buffer discharge ports are in respective fluid communication with a different one of the plurality of biocontainers. An amount of material stored within each one of the plurality of biocontainers is respectively sensed. A fill level signal indicative of a value for the amount of material sensed within each one of the plurality of biocontainers is respectively transmitting to a control unit. The control unit is used to identify the biocontainer with which the first buffer discharge port is in fluid communication based upon the change of the fill level signal therefrom.

Further and alternative aspects and features of the disclosed principles will be appreciated from the following detailed description and the accompanying drawings. As will be appreciated, the buffer management systems, dilution skids, and manifolds for use in a buffer management system disclosed herein are capable of being carried out in other and different embodiments, and capable of being modified in various respects. Accordingly, it is to be understood that both the foregoing general description and the following detailed description are exemplary and explanatory only and do not restrict the scope of the appended claims.

Figure 1:
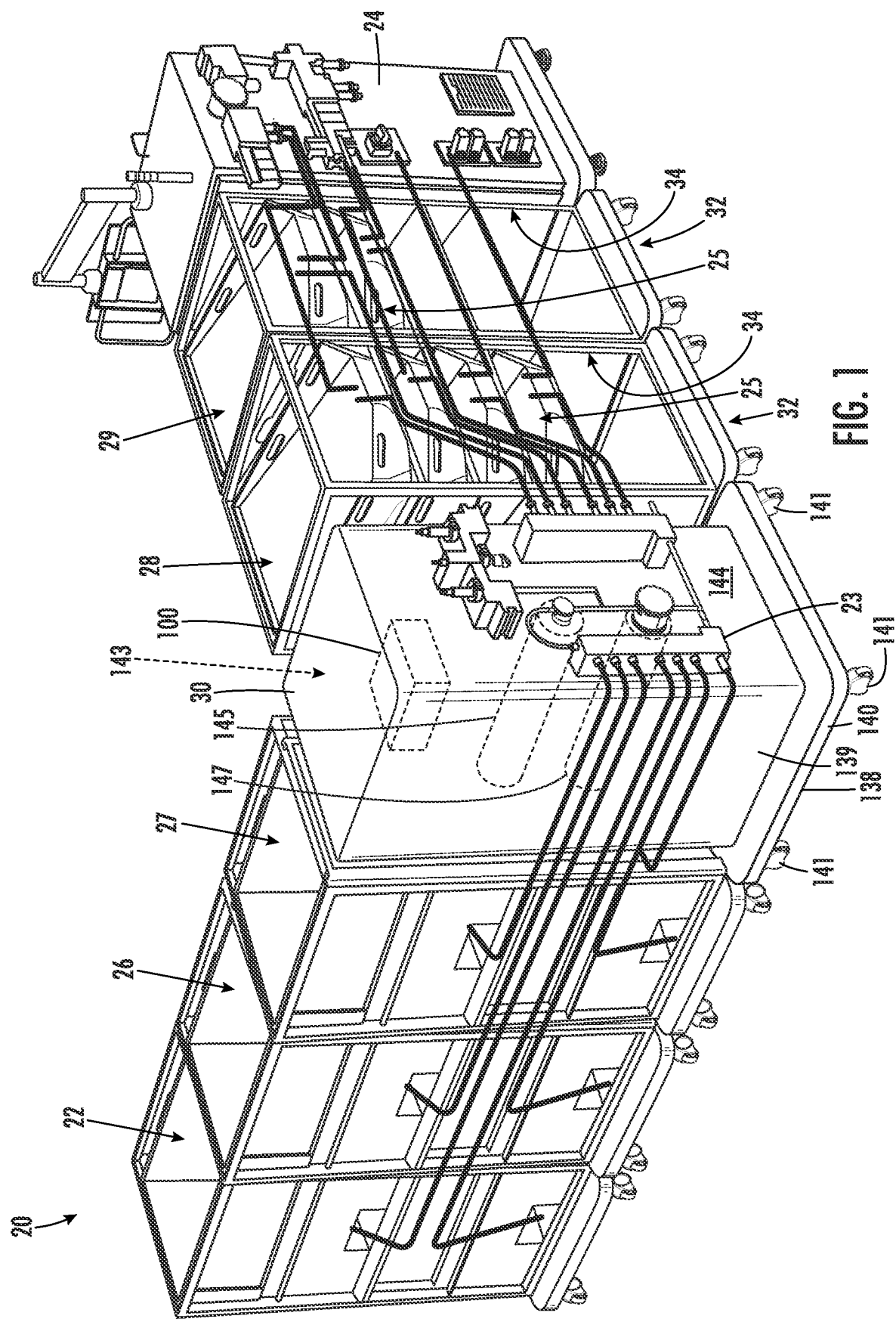
FIG. 1 is a perspective view of an embodiment of a buffer management system constructed in accordance with principles of the present disclosure that includes an embodiment of a manifold constructed in accordance with principles of the present disclosure and a bioprocessing unit.

It should be understood that the drawings are not necessarily to scale and that the disclosed embodiments are illustrated diagrammatically and in partial views. In certain instances, details which are not necessary for an understanding of this disclosure or which render other details difficult to perceive may have been omitted. It should be understood that this disclosure is not limited to the particular embodiments illustrated herein.

DETAILED DESCRIPTION OF THE INVENTION

Embodiments of a buffer management system constructed in accordance with principles of the present disclosure are adapted to be used in a bioprocessing system. Embodiments of a buffer management system constructed in accordance with principles of the present disclosure can include a supply of concentrated buffer solution, a dilution skid configured to selectively dilute the concentrated buffer solution such that the diluted buffer solution has a predetermined buffer characteristic, and a diluted buffer solution storage assembly configured to store a volume of at least one diluted buffer solution therein for use in a selected bioprocessing application. In embodiments, a dilution skid constructed according to principles of the present disclosure includes a single use manifold.

Embodiments of a buffer management system constructed in accordance with principles of the present disclosure can be used in biopharmaceutical environments, but can be used in other industrial applications where different fluids, solutions, reagents and/or chemicals are stored for metering to a process station. Embodiments of a buffer management system constructed in accordance with principles of the present disclosure can be used to selectively generate at least one buffer solution from a supply of concentrated buffer solution for use in a downstream processing application.

Embodiments of a buffer management system constructed in accordance with principles of the present disclosure are configured as a relatively compact storage solution to achieve a range of different buffer solutions for an intended use in a bioprocessing application. Embodiments of a buffer management system constructed in accordance with principles of the present disclosure can include a supply of concentrated buffer solution, a dilution skid with a single use manifold, and multiple biocontainer bags stacked in a small footprint (particularly relative to a conventional workstation configured for use in a similar bioprocessing application) for storing therein buffer solution diluted to a desired degree for use in a predetermined bioprocessing application. Embodiments of a buffer management system constructed in accordance with principles of the present disclosure can be used as a replacement for conventional systems using relatively larger storage totes for a comparable bioprocessing application.

Embodiments of a buffer management system constructed in accordance with principles of the present disclosure are configured to create buffer solutions by diluting buffer concentrates with WFI (water for injection). It should be understood that, as used herein and in embodiments according to principles of the present disclosure, WFI can also comprise any other liquid suitable for use in blending with another liquid for either dilution purposes or any other suitable blending operation. In embodiments, a buffer management system constructed in accordance with principles of the present disclosure are configured to produce buffer solutions using buffer concentrates with a dilution factor in a range from five times to twenty times to achieve the final, diluted buffer solution.

Embodiments of a buffer management system constructed in accordance with principles of the present disclosure are configured to receive concentrated buffer solutions (such as concentrated buffers in a range between five times and twenty times the concentration as desired buffer solution) and mixing them with a supply of WFI (water for injection) in a variable ratio to achieve the desired buffer solution. The diluted buffer solutions can be delivered to a storage area (such as a rack tower supporting a plurality of biocontainer bags for use in a bioprocessing application (such as a chromatography/tangential flow filtration (TFF) application, for example) on demand.

In embodiments, a manifold constructed according to principles of the present disclosure includes tubing, single use pump heads, sensors and connections configured to selectively blend at least one concentrated buffer solution with WFI to produce a diluted buffer solution within a predetermined tolerance for a given buffer characteristic (such as, e.g., pH or conductivity) or a combination of two or more buffer characteristics. In embodiments, a manifold constructed according to principles of the present disclosure includes two single use pump heads, one to deliver at least one buffer concentrate and the other to deliver the WFI for mixing with the buffer concentrate within the manifold to produce a diluted buffer solution according to a predetermined buffer recipe. In embodiments, the manifold is arranged with the control unit of the dilution skid to provide automated operation of the buffer management system by, for example, varying pump speeds/ratios in response to at least one sensor feedback loop to achieve a desired buffer recipe from a library of multiple buffer recipes, selectively operating the control valves according to a predetermined operating sequence, and interfacing with other units of operation to respond to demands for buffer solution.

In embodiments, a manifold constructed according to principles of the present disclosure includes a plurality of buffer inlet ports, a WFI inlet port, a pair of single use pump heads, at least one buffer characteristic sensor, a plurality of buffer discharge ports corresponding to the number of buffer inlet ports, and a waste outlet port. In embodiments, a manifold constructed according to principles of the present disclosure includes tubing arrangement configured to interact with a plurality of control valves such that a control unit can operate the control valves to close, open or redirect the flow of liquid through the manifold to perform a variety of buffer management sequences.

Figure 2:
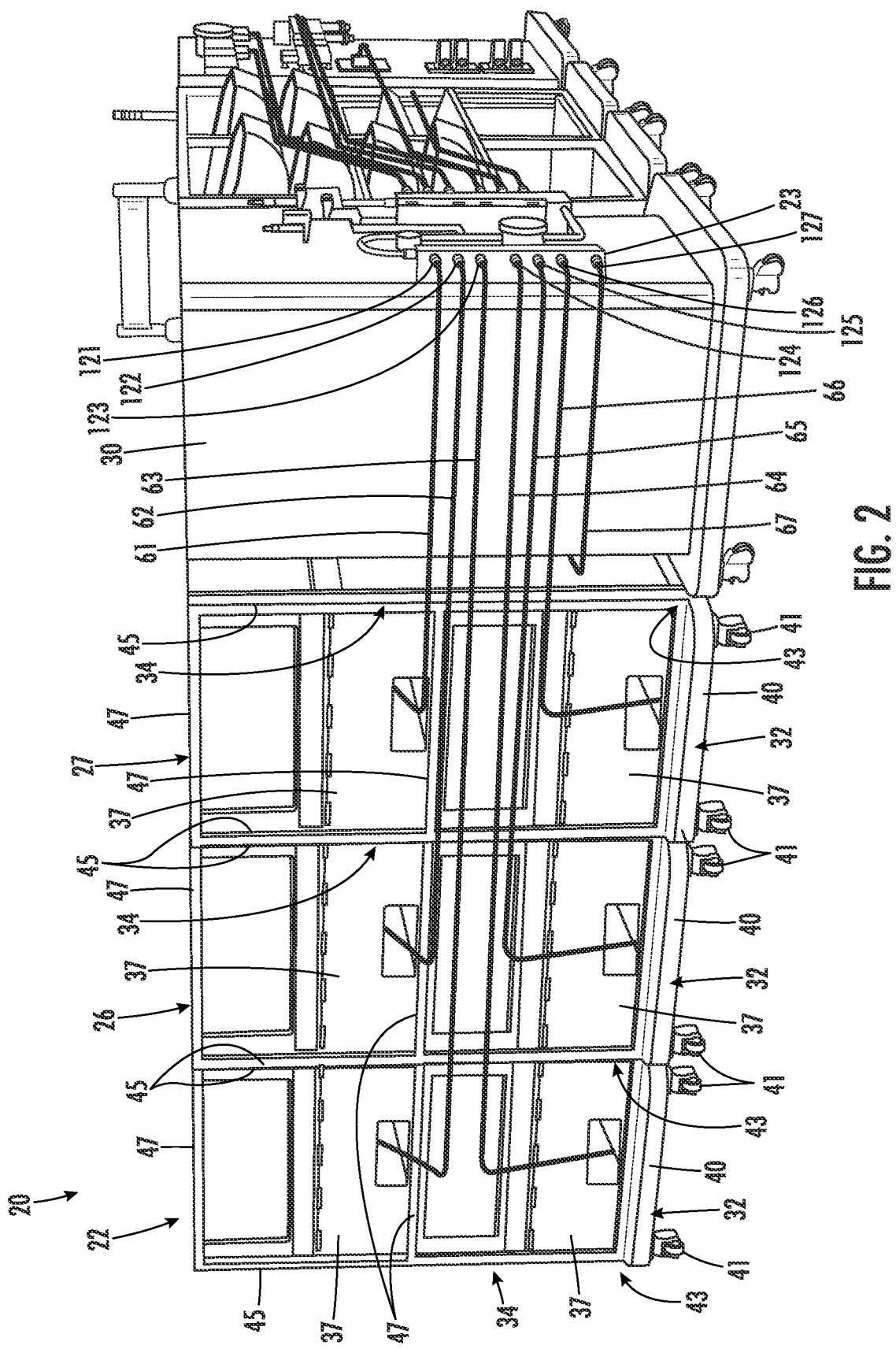
FIG. 2 is another perspective view of the buffer management system of FIG. 1 from a concentrated buffer solution side thereof.
Figure 3:
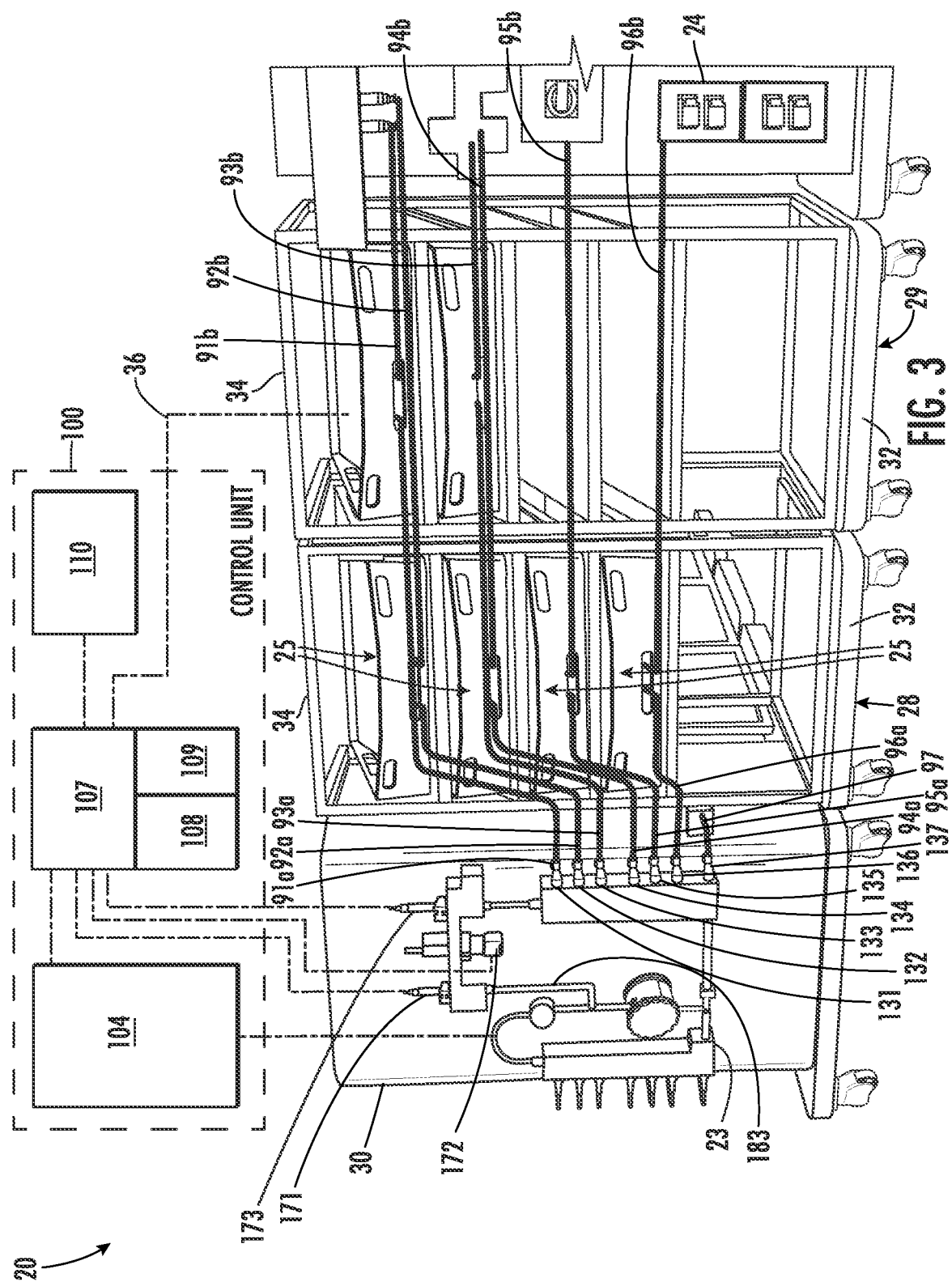
FIG. 3 is another perspective view of the buffer management system of FIG. 1 from a diluted buffer solution side thereof.

Turning now to the FIGURES, there is shown in FIGS. 1-3 an embodiment of a buffer management system 20 constructed in accordance with principles of the present disclosure that includes a dilution skid 30 constructed in accordance with principles of the present disclosure that includes a single use manifold 23. In embodiments, the buffer management system 20 can include at least one embodiment of a manifold 23 constructed according to principles of the present disclosure. The illustrated buffer management system 20 is configured to receive different concentrated buffer solutions (such as, buffer solutions in a range between five times and twenty times the concentration of the buffer solution for use in an intended bioprocessing application in a bioprocessing unit 24) and mixing them serially with a supply of WFI (water for injection) to a variable ratio to achieve the desired buffer. The buffer management system 20 can be configured to store the diluted buffer solutions for delivery to, and use by, a bioprocessing application (such as, chromatography, tangential flow filtration (TFF), etc.) performed on demand in the bioprocessing unit 24. In embodiments, the diluted buffer solution can be stored in a plurality of biocontainer assemblies 25.

In embodiments, the buffer management system 20 includes at least one workstation 22, 26, 27 configured to support a supply of concentrated buffer solution, the inline dilution skid 30 having the single use manifold 23, and at least one workstation 28, 29 configured to store diluted buffer solution made from the supply of concentrated buffer solution, which can be stored in biocontainer assemblies 25. In embodiments, the buffer management system 20 comprises a single use system configured to produce multiple buffers from concentrated buffer solutions. In embodiments, the buffer management system 20 includes multiple workstations 22, 26, 27 configured to support multiple, different concentrated buffers and multiple workstations 28, 29 configured to hold multiple surge biocontainer assemblies 25 configured to store the corresponding diluted buffer solutions made from the different supplies of concentrated buffer solutions via the inline dilution skid 30.

In the illustrated embodiment, the buffer management system 20 includes three concentrated buffer rack towers 22, 26, 27 configured to hold different supplies of concentrated buffer solutions, the inline dilution skid 30 configured to produce a plurality of diluted buffer solutions for use in a bioprocessing application in the bioprocessing unit 24, and a pair of diluted buffer rack towers 28, 29 configured to hold a supply of diluted buffer solutions. In other embodiments, the buffer management system 20 can include different equipment configured to hold the supply of concentrated buffer solutions and/or the diluted buffer solutions. For example, in other embodiments, a buffer management system 20 constructed according to principles of the present disclosure can include at least one tower 22, 26, 27 configured to hold one or more biocontainer assemblies filled with a concentrated buffer. In other embodiments, a buffer management system constructed according to principles of the present disclosure can include at least one tower 28, 29 configured to hold one or more tanks filled with a diluted buffer.

Referring to FIG. 2, the three concentrated buffer rack towers 22, 26, 27 of the illustrated buffer management system 20 have a similar construction. Each of the illustrated concentrated buffer rack towers 22, 26, 27 includes a trolley 32, a frame structure 34, and a pair of biocontainer totes 37. The frame structure 34 is mounted to the trolley 32 and is configured to support the pair of biocontainer totes 37 in a stacked relationship. The concentrated buffer rack towers 22, 26, 27 comprise workstations configured to hold concentrated buffer solutions for selective delivery to the inline dilution skid 30.

The trolley 32 includes a base 40 and a plurality of wheels 41 rotatably attached to the base 40. In the illustrated embodiment, the base 40 is rectangular, and there is a wheel 41 rotatably attached at each corner of the base 40. In embodiments, the base 40 can be substantially square-shaped. The base 40 of the trolley 32 is mounted to a bottom 43 of the frame structure 34.

The frame structure 34 is connected to the trolley 32. The frame structure 34 includes a plurality of uprights 45 connected to the trolley 32 and in spaced relationship to each other and a plurality of cross members 47 extending between two of the uprights 45 such that the frame structure 34 can support the biocontainer totes 37 in a vertical stacked relationship to each other. In the illustrated embodiment, each concentrated buffer rack tower 22, 26, 27 is configured to support two biocontainer totes 37 in a stacked relationship. In other embodiments, the concentrated buffer rack towers 22, 26, 27 can be configured to support a different number of biocontainer totes 37, including a single biocontainer tote 37.

Each of the biocontainer totes 37 is in fluid connection with the manifold 23 of the inline dilution skid 30 via respective flexible tubing lines 61, 62, 63, 64, 65, 66 extending between each biocontainer tote 37 and the manifold 23. In particular, the tubing extends between each biocontainer tote 37 and a respective one of a plurality of buffer inlet ports 121, 122, 123, 124, 125, 126 of the manifold 23. A water supply line 67 can be in fluid communication with a supply of WFI (water for injection) such that the water supply line 67 extends between the supply of WFI and a WFI inlet port 127 of the manifold 23. In embodiments, the flexible tubing 61, 62, 63, 64, 65, 66 can be made from any suitable material, such as, silicone, thermoplastic elastomer (TPE), etc. In embodiments, the tubing 61, 62, 63, 64, 65, 66 is adapted to be selectively occluded by a pinch valve externally mounted thereto.

In other embodiments, the concentrated buffer rack towers 22, 26, 27 of a buffer management system constructed according to principles of the present disclosure can have a different construction. For example, in embodiments, the concentrated buffer rack towers can include a plurality of biocontainer assemblies as described below in connection with the diluted buffer rack towers 28, 29 having a "2D" (or "two-dimensional") biocontainer bag, as is understood in the art.

Referring to FIG. 3, the pair of diluted buffer rack towers 28, 29 of the buffer management system 20 have a similar construction. Each of the illustrated diluted buffer rack towers 28, 29 includes a trolley 32, a frame structure 34, and a plurality of biocontainer assemblies 25. The frame structure 34 is mounted to the trolley 32 and is configured to support a number of the biocontainer assemblies 25. The diluted buffer rack towers 28, 29 comprise workstations configured to hold biocontainers 25 configured to act as surge containers.

The frame structure 34 can support a number of the bag fill level assemblies 35 in a vertical stacked relationship to each other. In the illustrated embodiment, each diluted buffer rack towers 28, 29 is configured to support four bag fill level assemblies 35 in a vertical stacked relationship to each other. In other embodiments, the diluted buffer rack towers 28, 29 can be configured to support a different number of bag fill level assemblies 35, including a single bag fill level assembly 35. The bag fill level assemblies 35 can include liquid level sensors which feedback to an automation control unit 100 of the dilution skid 30.

In the illustrated embodiment, each diluted buffer rack tower 28, 29 is configured to support up to four biocontainer assemblies 25 in a stacked relationship. In other embodiments, the diluted buffer rack tower 28, 29 can be configured to support a different number of biocontainer assemblies 25, including a single biocontainer assembly 25.

In embodiments, each of the biocontainer assemblies 25 includes at least one biocontainer 55 (see FIG. 4) that is in fluid connection with the manifold 23 of the inline dilution skid 30 via respective flexible tubing lines 91, 92, 93, 94, 95, 96 extending between each biocontainer 25 and the manifold 23 and each biocontainer assembly 25 and the bioprocessing unit 24. In particular, the tubing 91a, 92a, 93a, 94a, 95a, 96a extends between each biocontainer 25 of the diluted buffer rack towers 28, 29 and a respective one of a plurality of discharge ports 131, 132, 133, 134, 135, 136 of the manifold 23. The tubing 91b, 92b, 93b, 94b, 95b, 96b extends between each biocontainer 25 of the diluted buffer rack towers 28, 29 and the bioprocessing unit 24 for on-demand usage by the bioprocessing unit 24 to perform a bioprocessing application. A waste line 97 can be in fluid communication with a waste port 137 of the manifold 23 such that a waste flow can be discharged from the manifold to a suitable location (e.g., a separate tank or drain system). In embodiments, the flexible tubing 91, 92, 93, 94, 95, 96, 97 can be made from any suitable material, such as, silicone, TPE, etc. In embodiments, the tubing 91, 92, 93, 94, 95, 96, 97 is adapted to be selectively occluded by a pinch valve externally mounted thereto.

Figure 4:
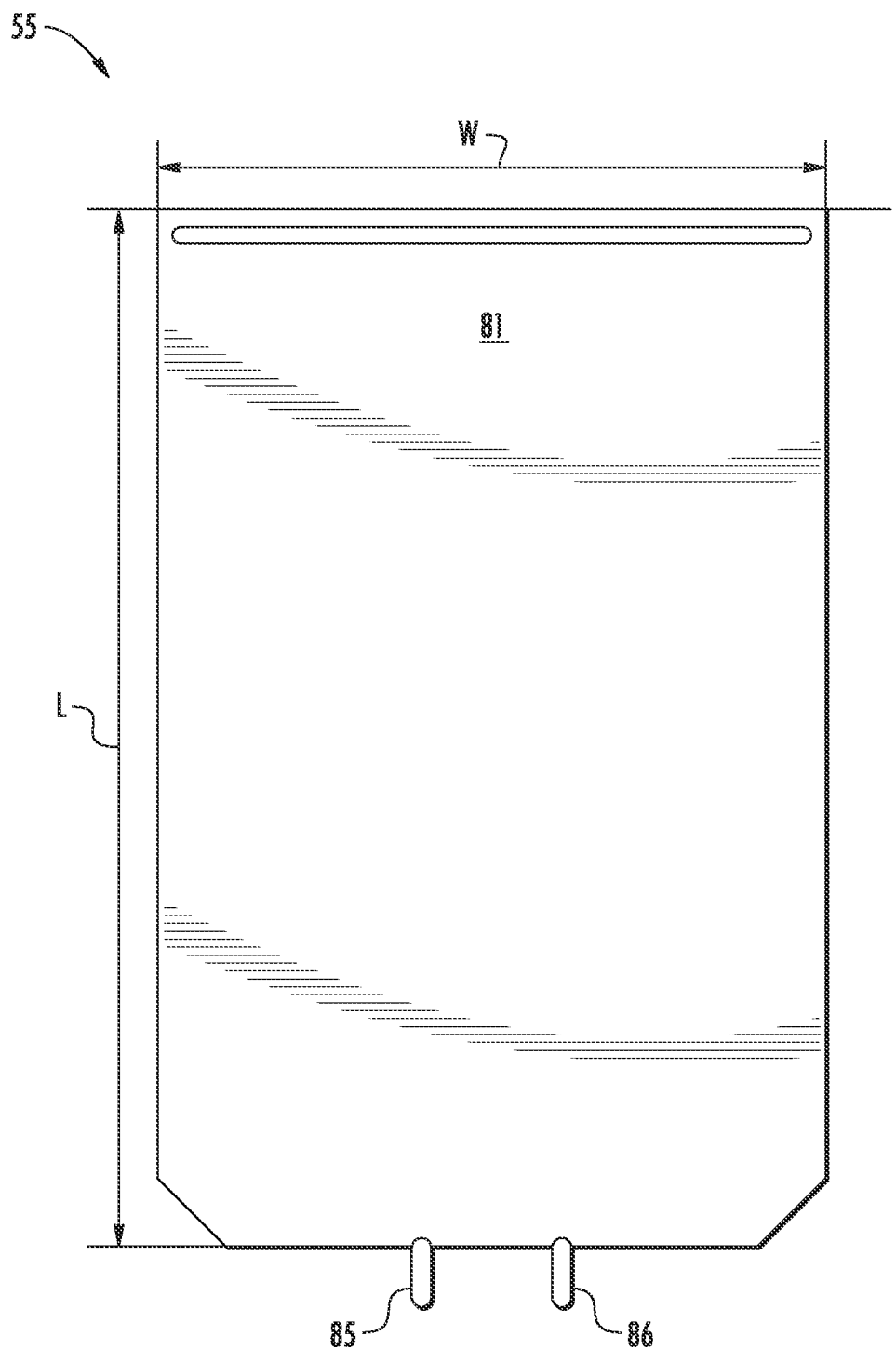
FIG. 4 is a plan view of an embodiment of a biocontainer bag suitable for use in embodiments of a buffer management system constructed in accordance with principles of the present disclosure.
Figure 5:
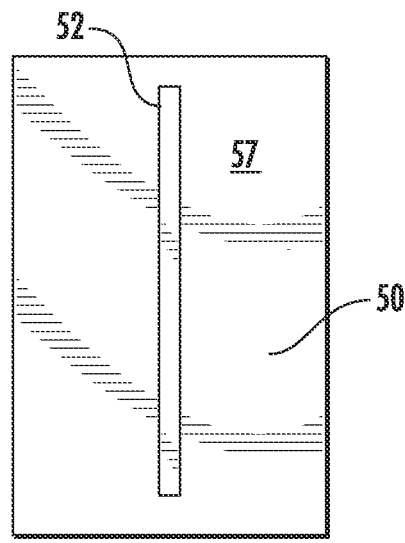
FIG. 5 is a top plan schematic view of an angled support member and a capacitive fill level sensor for use in embodiments of a biocontainer assembly of a buffer management system constructed in accordance with principles of the present disclosure.
Figure 6:
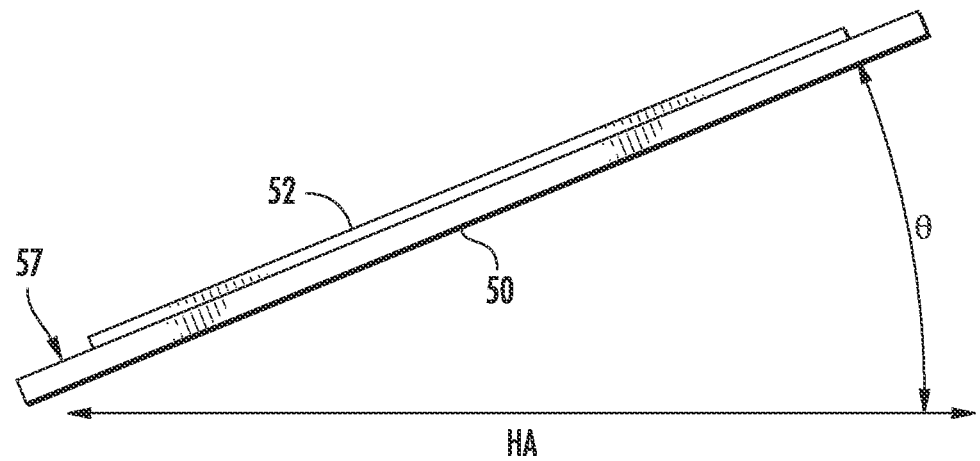
FIG. 6 is a side elevational view of the angled support member and the capacitive fill level sensor of FIG. 5.

Referring to FIGS. 4-6, in embodiments, each biocontainer assembly 25 includes a support member 50 in the form of an angled shelf mounted to the frame structure 34 of one of the diluted buffer rack towers 28, 29, an electronic fill level sensor 52, and a biocontainer bag 55. In embodiments, the angled support member 50 includes a support surface 57 configured to support the biocontainer bag 55 in an inclined storage position with respect to a horizontal axis HA. In the illustrated embodiment, the frame structure 34 of each diluted buffer rack tower 28, 29 includes a series of angled shelves 50, pitched at an incline angle $\Theta$ to a horizontal axis HA. The lower edge of each shelf 50 is positioned at a front end of the frame structure 34. The upper edge of each shelf 50 is positioned at a rear end of the frame structure 34, which is in opposing relationship to the front end of the frame structure 34.

In embodiments, the fill level sensor 52 is configured to generate a fill level signal indicative of the volume of material within the storage volume of the biocontainer bag 55 as detected by the fill level sensor 52. In embodiments, the fill level sensor 52 comprises a capacitive fill level sensor.

Referring to FIG. 4, in embodiments, the biocontainer bag 55 comprises any suitable container configured to store a predetermined volume of material for use in an intended application. In embodiments, the biocontainer bag 55 comprises a "2D" (or "two-dimensional") biocontainer bag, as is understood in the art, in which the width W and length L of the biocontainer bag 55 determine how the fill level moves up the biocontainer bag 55 and is detected by the fill level sensor 52.

In the illustrated embodiment, the biocontainer bag 55 comprises a 2D biocontainer bag made from a flexible film material. The biocontainer bag 55 can include two or more ports 85, 86 and tubing with connector ends that are configured to receive material within the interior storage volume of the bag 55 and/or discharge material from the bag 55. In other embodiments, the biocontainer bag 55 includes at least one other port configured for use as a sampling port. In embodiments, the biocontainer bag 55 can define therein a storage volume of a predetermined size, such as one hundred liters, for example. In other embodiments, the storage volume can be a different size. In embodiments, the biocontainer bag 55 comprises a suitable commercially-available single use biocontainer bag, such as, for example, those available from Pall Corporation of Port Washington, N.Y., under the brand name Allegro™ 2D biocontainer bags.

In embodiments, the biocontainer bag 55 can include at least a pair of flexible panels 81 that are connected together. The flexible panels 81 cooperate together to define an interior storage volume that is configured to hold a predetermined volume of material (e.g., one hundred liters). In embodiments, each panel 81 is made from a suitable plastic material. For example, in embodiments, each panel 81 is made of a low density polyethylene (LDPE) fluid contact and external film with an ethylene-vinyl alcohol copolymer (EvOH) gas barrier internal film. In embodiments, the biocontainer bag 55 can be made from a material that satisfies the requirements of at least one of: the USP <88> Biological Reactivity Tests, in vivo, for Class VI-50° C. Plastics that target-monitor the effect of the biocontainer's extracts for their systemic toxicity, tissue irritation, and biocompatibility for implantation; USP <87> Biological Reactivity Tests (in vitro) for plastics (cytotoxicity); and ISO 10993 Biological Evaluation of a Medical Device (Section 8.2.2: ISO 10993 Biological Evaluation of Medical Devices) in Section 4 (Hemolysis), Section 5 (Cytotoxicity), Section 6 (Implantation Test), Section 10 (Irritation and Sensitization Test), and Section 11 (Acute Systemic Toxicity).

Referring to FIGS. 5 and 6, in embodiments, each shelf 50 is configured to support a biocontainer bag 55 of a predetermined size. The angled support 50 includes a support surface 57 configured to support the biocontainer bag 55 in an inclined storage position with respect to a horizontal axis HA. In embodiments of a biocontainer assembly 25, the capacitive fill level sensor 52 is mounted to the support member 50 in any suitable manner which permits the fill level sensor 52 to detect the volume of material stored within a biocontainer bag 55 supported by the support member 50. The capacitive fill level sensor 52 can be mounted to the angled support member 50 such that the capacitive fill level sensor 52 is positioned to detect a volume of liquid disposed within the biocontainer bag 55 when the biocontainer bag 55 is in an inclined storage position over a range of liquid volumes between a predetermined minimum fill volume and a predetermined maximum fill volume.

The support surface 57 of the shelf 50 is generally planar and is disposed at an incline angle Θ with respect to the horizontal axis HA. In the illustrated embodiment, the incline angle Θ is twenty-five degrees. In embodiments, the incline angle Θ of a support member 50 of a biocontainer assembly can vary. In embodiments, the support surface 57 of the support member 50 of a biocontainer assembly can be disposed at an incline angle Θ with respect to the horizontal axis HA where the incline angle Θ is in a range between five degrees and forty-five degrees, in a range between ten degrees and forty degrees in other embodiments, in a range between fifteen degrees and thirty-five degrees in yet other embodiments, and in a range between twenty degrees and thirty degrees in still other embodiments. In embodiments, the support surface 57 of the support member 50 of a biocontainer assembly constructed according to principles of the present disclosure can be disposed at an incline angle Θ with respect to the horizontal axis where the incline angle Θ is in a range between twenty degrees and twenty-eight degrees, and in a range between twenty-two degrees and thirty degrees in still other embodiments. In embodiments, the support member 50 can be made from any suitable material, such as a suitable plastic or metal, for example.

One of ordinary skill in the art will appreciate that the incline angle Θ can be varied according to the specific parameters of the application within which the biocontainer assembly is intended to be used. For example, a shallow angle can be used in applications in which the range of liquid volume desired to be monitored is less than the maxim fill volume of the biocontainer bag being used in the biocontainer assembly. A steeper incline angle can be used in embodiments in which the resolution of the fill level sensor strip 52 is enhanced and/or it is desired to monitor smaller changes in volume.

In embodiments, each shelf 50 has associated therewith at least one electronic fill level sensor 52. In embodiments, the fill level sensor 52 is configured to generate a fill level signal indicative of the amount of material within the storage volume of the biocontainer bag 55 as detected by the fill level sensor 52. In embodiments, the capacitive fill level sensor 52 can be used to measure the fill level of fluid media or of solid materials disposed within the storage volume of the biocontainer bag 55. In embodiments, the capacitive fill level sensor 52 can be a suitable commercially-available strip sensor, such as those available from Balluff Ltd., which can detect fill levels along the strip over a predetermined length, such as, e.g., 850 mm. In embodiments, the capacitive fill level sensor 52 for measuring fill levels can be configured to develop a measurement impedance in response to being within detection proximity of the material stored within the biocontainer bag 55, the ohmic component of which, particularly the capacitive component of which, reflects a measure for the fill level of the material within the biocontainer bag 55 and which can be used to generate the fill level signal.

In embodiments, the capacitive fill level sensor 52 includes an electrode unit having a strip-shaped measurement electrode, a strip-shaped counter electrode and a strip-shaped shielding electrode. In embodiments, the shielding electrode at least partially surrounds the measurement electrode. A first AC voltage source having a predefined frequency and amplitude is provided, to which the shielding electrode is connected such that a shielding capacitor formed between the shielding electrode and the measurement electrode has a shielding capacitance that is proportional to the length of the shielding electrode. A second AC voltage source of equal frequency and a predefined second amplitude is provided. The second amplitude is in phase opposition to the first amplitude, to which AC voltage source the counter electrode is connected, such that a measurement capacitor formed between the counter electrode and the measurement electrode has a measurement capacitance that is proportional to the fill level. The measurement electrode voltage present at the measurement electrode is used to determine the fill level. In embodiments, the capacitive fill level sensor 52 can be similar in other respect to the sensors disclosed in U.S. Patent Application Publication No. US2016/0047683, which is entitled, "Capacitive Fill Level Sensor," and which is incorporated herein in its entirety.

In embodiments, the fill level sensor 52 can be mounted directly to the support surface 57 of the shelf 50. In yet other embodiments, the fill level sensor 52 can be mounted to the underside of the support member 50.

In other embodiments, the capacitive fill level sensor 52 can be replaced with multiple fill level sensors arranged in a matrix and positioned at discrete positions corresponding to a desired control sequence. In embodiments, the multiple fill level sensors can operate as on-off type sensors that provide a fill level signal indicative of a certain volume of liquid within the biocontainer bag 55 that can be used to manage the buffer solutions (e.g., a maximum fill position, a minimum fill position, and operational fill levels).

In embodiments, the biocontainer assemblies 25 can be variable depending on the biocontainer maximum volume requirements. In other embodiments, the shelf 50 can be configured to support a plurality of biocontainer bags 55 with each such biocontainer bag 55 having associated therewith a respective electronic fill level sensor 52 mounted to the shelf 50.

In other embodiments, the biocontainer assembly 25 includes a different type of fill level sensor. For example, in other embodiments, the biocontainer assembly 25 can include a weigh scale to determine the weight of the buffer solution within the respective one of the biocontainer bags 55. The measured weight of the buffer solution can be converted into a volume measurement for such liquid. In embodiments, the weigh scale comprises a suitable load cell which generates an electrical signal indicative of the measured weight.

Referring to FIG. 1, the inline dilution skid 30 includes a trolley 138, a cabinet 139, and the single use manifold 23. The cabinet 139 is mounted atop the trolley 138 and is configured to house hydraulic and automation equipment of the buffer management system 20. The manifold 23 comprises a single use manifold that is removably mounted to the cabinet 139 such that the manifold 23 is in operable arrangement with the hydraulic and automation equipment inside the cabinet 139.

The trolley 138 includes a base 140 and a plurality of wheels 141 rotatably attached to the base 140. In the illustrated embodiment, the base 140 is rectangular, and there is a wheel 141 rotatably attached at each corner of the base 140. In embodiments, the base 140 can be substantially square-shaped.

The cabinet 139 is mounted to the base 140 of the trolley 138. In embodiments, the cabinet 139 comprises a storage unit for the automation equipment and is made from a suitable metal, such as stainless steel, for example. The cabinet 139 defines an interior cavity 143 and having an exterior surface 144. In embodiments, the cabinet 139 houses therein the control unit 100 and a pair of pump bodies comprising a buffer pump body 145 and a WFI pump body 147. A plurality of hydraulic control valves 151-167 (see FIG. 7) can also be supported by the cabinet 139.

Referring to FIG. 1, the buffer pump body 145 and the WFI pump body 147 are disposed within the interior cavity 143 of the cabinet 139. The single use manifold 23 is removably mounted to the exterior surface 144 of the cabinet 139 such that the manifold 23 is in operable arrangement with the buffer pump body 145 and the WFI pump body 147.

Figure 7:
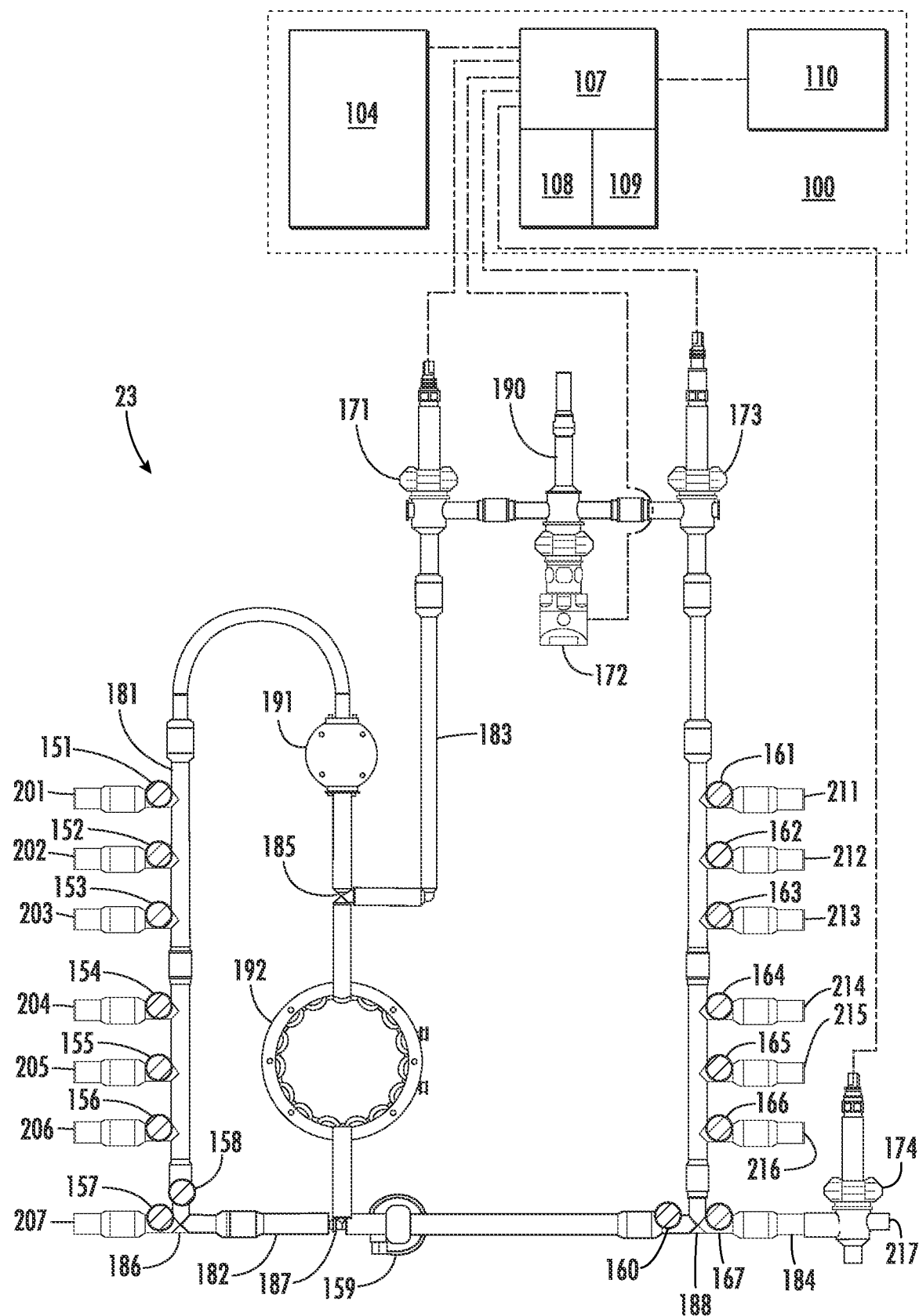
FIG. 7 is an elevational view of the manifold of FIG. 1 that is suitable for use in embodiments of a buffer management system constructed in accordance with principles of the present disclosure.

In embodiments, the manifold 23 is configured to be operably arranged with the buffer pump body 145, the WFI pump body 147, and the control unit 100 stored within the cabinet 139 and with the control valves 151-167 (see FIG. 7). The manifold 23 is configured to selectively mix a supply of at least one concentrated buffer solution with a supply of WFI to produce a buffer solution having a desired buffer characteristic for use in a bioprocessing application. After use in the intended bioprocessing application, the manifold 23 can be disconnected from the cabinet 139 of inline dilution skid 30 and replaced with another single use manifold having a similar construction.

Referring to FIG. 1, the pumps 145, 147 are in operable relationship with the control unit 100 such that the control unit 100 can selectively operate the pumps 145, 147. The buffer pump 145 is configured to deliver a supply of at least one of the concentrated buffers stored in the concentrated buffer rack towers 22, 26, 27 through the manifold 23, and the WFI pump 147 is configured to deliver a supply of WFI through the manifold 23. In embodiments, the pumps 145, 147 can be any suitable pump capable of producing a flow of liquid that meets the specification of the intended application. In embodiments, the buffer pump 145 and the WFI pump 147 comprise variable displacement pumps.

In embodiments, the buffer concentrates can be made in a range of strengths from five times to at least twenty times or more. As a result, proportionally the WFI is pumped at a greater volume than the buffer concentrate(s) in order to achieve the desired diluted buffer recipe. Accordingly, in embodiments, the buffer pump 145 and the WFI pump 147 are sized to meet the respective specified flow demands of the various diluted buffer recipes that are intended to be used with the buffer management system 20. In embodiments, the buffer management system 20 is configured to produce up to 1,200 liters per hour, but varying system sizes can be provided in yet other embodiments.

The control unit 100 is in electrical communication with the buffer pump body 145 and the WFI pump body 147. The control unit 100 is configured to selectively operate the buffer pump body 145 and the WFI pump body 147. In the illustrated embodiment, the control unit 100 is configured to independently operate the buffer pump 145 and the WFI pump 147. In embodiments, the control unit 100 is configured to control at least one of a pump speed and a volume displacement of at least one of the buffer pump body 145 and the WFI pump body 147 to adjust a volumetric ratio of a buffer solution and an amount of water for injection (WFI) being blended together in the manifold 23.

The control unit 100 is configured to selectively operate the pumps 145, 147 according to at least one input signal received from the manifold 23 and the biocontainer assemblies 25 of the diluted buffer rack towers 28, 29 to provide a plurality of buffer management operations. In embodiments, the control unit 100 is configured to operate the inline dilution skid 30 to perform at least one buffer management sequence.

Referring to FIG. 3, in embodiments, the control unit 100 includes a controller 104, a processor 107, a non-transitory computer readable medium 108 bearing a buffer management program, a data storage device 109, and a display device 110. The controller can be configured to selectively operate at least one component of the buffer management system 20, such as the buffer pump body 145 and the WFI pump body 147, for example. The controller is in operable communicative arrangement with the processor 107. The processor 107 is in operable arrangement with the non-transitory computer-readable medium 108 to execute the buffer management program contained thereon. The processor 107 is in operable arrangement with the display device 110 to selectively display output information from the buffer management program and/or to receive input information from a graphical user interface displayed by the display device 110.

In embodiments, the controller 104 can include a user input and/or interface device having one or more user actuated mechanisms (e.g., one or more push buttons, slide bars, rotatable knobs, a keyboard, and a mouse) adapted to generate one or more user actuated input control signals. In embodiments, the controller 104 can be configured to include one or more other user-activated mechanisms to provide various other control functions for the buffer management system, as will be appreciated by one skilled in the art. The controller 104 can include a display device adapted to display a graphical user interface. The graphical user interface can be configured to function as both a user input device and a display device in embodiments. In embodiments, the display device can comprise a touch screen device adapted to receive input signals from a user touching different parts of the display screen. In embodiments, the controller 104 can be in the form of a smart phone, a tablet, a personal digital assistant (e.g., a wireless, mobile device), a laptop computer, a desktop computer, or other type of device. In embodiments, the controller 104 and the processor 107 can comprise the same device or set of equipment.

In embodiments, the processor 107 comprises a specially programmed processor that can be used to determine whether the buffer solution being produced through the inline dilution skid is within a predetermined tolerance for a given desired buffer solution based upon the buffer solution data sent to the processor 107 by the manifold 23. In the illustrated embodiment, the processor 107 is in operable arrangement with the controller 104 to facilitate the control and the operation of the buffer management system 20. In embodiments, the processor 107 can be configured to receive input signals from the controller 104, to send input control signals to the controller 104, and/or to send output information to the controller 104. In embodiments, the controller 104 and the processor 107 can comprise the same device.

In embodiments, at least one sensor 171, 172, 173 is associated with a discharge line 183 of the manifold 23 and is configured to sense a value of a buffer characteristic (such as, conductivity or pH, e.g.) or fluid parameter, to generate a signal indicative of the sensed value for the buffer characteristic/fluid parameter, and to transmit the signal to the control unit 100. In embodiments, the control unit 100 can use the received signal to control the operation of the buffer management system 20. Each sensor 171, 172, 173 is in electrical communication with the control unit 100 to transmit the respective signal thereto. In embodiments, the control unit 100 is configured to control the operation of at least one of the buffer pump body 145 and the WFI pump body 147 based upon the signal received from at least one such sensor 171, 172, 173.

In embodiments, the sensor 171, 172, 173 can be any suitable sensor configured to detect a parameter of a buffer solution. In embodiments, the buffer parameter can be used to determine whether the buffer solution being produced is within a specified tolerance range for a desired buffer solution and/or is within a desired operational range for a desired fluid characteristic. In the illustrated embodiment, the single use manifold 23 includes a conductivity sensor 171, a pressure sensor 172, and a pH sensor 173 that are disposed in the discharge line 183 of the manifold 23 and that are respectively configured to transmit a conductivity signal, a pressure signal, and a pH signal to the control unit 100. In embodiments, the buffer management program can use at least one of the conductivity signal and the pH signal to determine whether the buffer solution passing through the discharge line is within a predetermined tolerance range of a given specification for a desired buffer. In embodiments, the buffer management program can use the pressure signal to determine whether the manifold 23 is operating below a predetermined maximum pressure for safe operation.

The processor 107 is in operable arrangement with the manifold 23 to receive the buffer solution data therefrom and with the diluted buffer rack towers 28, 29 to receive buffer solution usage data therefrom. Although one electrical communication line is shown extending between the processor 107 and the diluted buffer rack towers 28, 29, it should be understood that in embodiments each biocontainer assembly of the diluted buffer rack towers 28, 29 can be in independent communication with the processor 107. In embodiments, the processor 107 is in electrical communication with the manifold 23, the diluted buffer rack towers 28, 29, and the concentrated buffer rack towers 22, 26, 27 via any suitable technique, including a wired communication channel. In embodiments, the processor 107 is in electrical communication with at least one of the manifold 23, the diluted buffer rack towers 28, 29, and the concentrated buffer rack towers 22, 26, 27 via a wireless communication network, including a Wi-Fi network and connected internet of things (IoT) devices throughout the buffer management system 20.

In embodiments, the processor 107 is configured to display in the display device 110 the buffer solution data received from the manifold and/or the rack towers 22, 26, 27, 28, 29. The buffer solution data can also be stored in the data storage device 109 operably arranged with the processor 107, and/or to correlate the buffer solution data with a predetermined buffer characteristic, such as, for example, its pH, to identify the buffer solution passing through the manifold and/or to determine whether the buffer solution being produced through the manifold is within a predetermined tolerance for a desired buffer solution.

In embodiments, the processor 107 can comprise any suitable computing device, such as, a microprocessor, a mainframe computer, a digital signal processor, a portable computing device, a personal organizer, a device controller, a logic device (e.g., a programmable logic device configured to perform processing functions), a digital signal processing (DSP) device, or a computational engine within an appliance. In embodiments, the processor 107 also includes one or more additional input devices (e.g., a keyboard and a mouse or other suitable human machine interface (HMI)).

The processor 107 can have one or more memory devices associated therewith to store data and information. The one or more memory devices can include any suitable type, including volatile and non-volatile memory devices, such as RAM (Random Access Memory), ROM (Read-Only Memory), EEPROM (Electrically-Erasable Programmable Read-Only Memory), flash memory, etc. In one embodiment, the processor 107 is adapted to execute programming stored upon a non-transitory computer readable medium to perform various methods, processes, and modes of operations in a manner following principles of the present disclosure.

The buffer management program is configured to determine whether the buffer solution being produced through the manifold 23 is within a predetermined tolerance for a given, desired buffer solution based upon the measurement signals received by the processor 107 from the manifold 23. In embodiments, the buffer management program is configured to use a pH signal from the pH sensor 173 of the manifold 23 to determine whether the buffer solution being produced is within a predetermined tolerance of the nominal specification provided for a given, desired buffer solution. In embodiments, the buffer management program is configured to use a conductivity signal from the conductivity sensor 171 of the manifold 23 to determine whether the buffer solution being produced is within a predetermined tolerance of the nominal specification provided for a given, desired buffer solution.

In embodiments, the non-transitory computer readable medium 108 can contain a buffer management program that is configured to implement an embodiment of a method of managing buffer solution according to principles of the present disclosure. In embodiments, the buffer management program includes a graphical user interface that can be displayed by the display device 110. The graphical user interface can be used to facilitate the inputting of commands and data by a user to the buffer management program and to display outputs generated by the buffer management program.

The buffer management program can be stored upon any suitable computer-readable storage medium. For example, in embodiments, a buffer management program following principles of the present disclosure can be stored upon a hard drive, floppy disk, CD-ROM drive, tape drive, zip drive, flash drive, optical storage device, magnetic storage device, and the like.

In embodiments, the pH and conductivity data from the manifold 23 can be displayed by the buffer management program via the graphical user interface in the display device 110. In embodiments, an operator can set a predetermined tolerance range for the pH and/or the conductivity, and the buffer management program can be configured to generate an alarm when at least one of the measured pH and the conductivity falls outside of a predetermined tolerance range. In embodiments, the alarm can be any suitable alarm including an audible signal and/or a warning message displayed via the graphical user interface on the display device 110.

In embodiments, the processor 107 is in operable communication with the data storage device 109 which includes at least one database containing buffer solution data. In embodiments, the buffer management program can be configured to store the measurement data generated by the manifold and the buffer solution data generated by the rack towers in the data storage device 109. In embodiments, the measurement data and buffer solution usage data can be associated in a logical manner with time data in the data storage device such that the various data can be retrievable for a given time.

Referring to FIG. 7, there is shown an embodiment of a manifold 23 constructed according to principles of the present disclosure that is suitable for use in embodiments of a buffer management system 20 constructed in accordance with principles of the present disclosure. The manifold 23 illustrated in FIG. 7 comprises a single use inline buffer dilution manifold. The manifold 23 is configured to be removably mounted to the inline dilution skid 30 of the buffer management system 20 of FIG. 1. In the illustrated embodiment, the manifold 23 comprises a replaceable part that is installed once in the inline buffer skid 30 for use in a bioprocessing application and uninstalled thereafter for disposal thereof.

In the illustrated embodiment, the manifold 23 includes a tubing arrangement that has a buffer inlet line 181, a WFI inlet line 182, the discharge line 183, and a waste line 184. The tubing arrangement interconnects the various ports 201-207, 211-217 of the manifold 23 and is associated with the control valves 151-167 to control the flow of buffer solution and WFI through the manifold 23. In embodiments, the tubing arrangement comprises a plurality of flexible tubing lines. In embodiments, the flexible tubing can be made from any suitable material, such as, silicone, TPE, etc. In embodiments, the buffer inlet line 181, the WFI inlet line 182, the discharge line 183, and the waste line 184 comprise tubing adapted to be selectively occluded by a pinch valve externally mounted thereto.

The buffer inlet line 181 is in fluid communication with a mixing junction 185. The WFI inlet line 182 is in fluid communication with the mixing junction 185, as well, such that the buffer inlet line 181 and the WFI inlet line 182 are in fluid communication with each other via the mixing junction 185. In the illustrated embodiment, the mixing junction 185 is in the form of a "T" piece.

In embodiments, the buffer inlet line 181 includes at least one buffer inlet port 201-06 in fluid communication therewith. In the illustrated embodiment, the manifold 23 includes six buffer inlet ports 201-06 that are in fluid communication with the buffer inlet line 181. A control valve 151-56 is respectively interposed between each of the buffer inlet ports 201-06 and the buffer inlet line 181 to selectively control the flow of concentrated buffer solution through each one of the buffer inlet ports 201-06 into the buffer inlet line 181.

A buffer drain junction 186 is in fluid communication with, and interposed between, the buffer inlet line 181 and the WFI inlet line 182. The buffer inlet line 181 extends between the buffer drain junction 186 and the mixing junction 185.

A control valve 157, 158 is respectively disposed upstream of the buffer drain junction 186 in both the WFI inlet line 182 and the buffer inlet line 181. The buffer drain control valve 158 can be selectively operated to permit the buffer inlet line 181 to be in fluid communication with the waste line 184 (via the WFI inlet line 182) for a buffer draining operation. The WFI inlet control valve 157 can be selectively operated to control the flow of WFI through the WFI inlet line 182.

The WFI inlet line 182 includes a water port 207 in fluid communication therewith. In embodiments, the WFI inlet port 207 can be fluidly connected to a suitable WFI source. In embodiments, the WFI source can comprise a tank of WFI. In embodiments, the WFI is produced using an on-site WFI generation system using at least one of multiple-effect distillation and vapor compression.

The WFI inlet line 182 extends between the water port 207 and the mixing junction 185. The WFI inlet line 182 is in fluid communication with the waste line 184 via a WFI drain junction 187. The WFI drain junction 187 is interposed between the water inlet port 207 and the mixing junction 185. The WFI drain junction 187 is in fluid communication with both the WFI inlet line 182 and the waste line 184 such that the WFI inlet line 182 is in fluid communication with the waste line 184 via the WFI drain junction 187. A first waste control valve 159 is disposed downstream of the WFI drain junction 187 in the waste line 184 to selectively block the flow of fluid from the WFI inlet line 182 to the waste line 184.

The discharge line 183 is in fluid communication with both the buffer inlet line 181 and the WFI inlet line 182 via the mixing junction 185. The discharge line 183 is in fluid communication with the waste line 184 via a discharge drain junction 188. The discharge line 183 extends between the mixing junction 185 and the discharge drain junction 188. The discharge drain junction 188 is in fluid communication with the discharge line 183 and the waste line 184. Second and third waste control valves 160, 167 are respectively disposed upstream and downstream of the discharge drain junction 188 in the waste line 184. The buffer inlet line 181 is in fluid communication with the waste line 184 via the buffer drain junction 186, the WFI line 182, and the WFI drain junction 187.

In embodiments, the discharge line 183 includes at least one buffer discharge port 211-16 in fluid communication therewith. In the illustrated embodiment, the manifold 23 includes six buffer discharge ports 211-216 that are in fluid communication with the discharge line 183. In embodiments, the number of discharge ports 211-216 corresponds to the number of buffer inlet ports 201-206. A control valve 161-166 is interposed between each of the buffer discharge ports 211-16 and the discharge line 183 to selectively control the flow of diluted buffer solution through each one of the buffer discharge ports 211-216 out of the manifold to the diluted buffer rack towers 28, 29.

In the illustrated embodiment, the discharge line also has in fluid communication therewith an integrity test line 190. In embodiments, the integrity test line 190 can be used to conduct other suitable sampling and testing of the buffer solution being produced as will be appreciated by one skilled in the art. In embodiments, pressurized air can be introduced into the manifold 23 via the integrity test line 190 to conduct a pressure decay test, which will give an indication if the manifold 23 is integral.

The waste line 184 is in fluid communication with the WFI inlet line 182 via the WFI drain junction 187 and the discharge line 183 via the discharge drain junction 188. The waste line 184 is in fluid communication with the buffer inlet 181 line via the buffer drain junction 186, the WFI line 182, and the WFI drain junction 187. A waste outlet port 217 is in fluid communication with the waste line 184. In embodiments, fluid can be discharged from the waste line 184 out through the waste outlet port 217 into a suitable tank or facility drain.

In the illustrated embodiment, the waste line 184 extends between the WFI drain junction 187 and the waste outlet port 217. The waste line 184 has associated therewith three control valves 159, 160, 167 to selectively occlude the waste line 184. The first and second waste control valves 159, 160 can be used to selectively occlude the portion of the waste line 184 that fluidly connects the buffer inlet line 181 and the WFI inlet line 182 to the waste outlet port 217. The third waste control valve 167 can be used to selectively occlude the portion of the waste line 184 downstream of the discharge drain junction 188. In embodiments, each of the ports 201-207, 211-217 has a respective one of the plurality of control valves 151-157, 161-167 in operable relationship therewith to selectively occlude the respective one of the buffer inlet ports 201-206, the WFI inlet port 207, the buffer discharge ports 211-216, and the waste outlet port 217 via the control unit 100.

In embodiments, the control valves 151-167 can be any type of control valve suitable for selectively controlling the flow of fluid through the manifold 23 as further discussed below. For example, in embodiments, the control valves 151-167 comprise pinch valves that are configured to selectively occlude the orifice within each flexible tubing line at the point of contact between the pinch valve and the tubing. The control valves 151-67 are in operable arrangement with the control unit 100 such that the control unit 100 can selectively operate the control valves 151-67. In the illustrated embodiment, the control unit 100 is configured to independently operate each control valve 151-167.

In the illustrated embodiment, the manifold 23 includes a buffer pump head 191 and a WFI pump head 192. The buffer pump head 191 is disposed in the buffer inlet line 181 and is configured to be operably arranged with the buffer pump body 145 in the cabinet 139 of the inline dilution skid 30 to selectively generate a fluid displacement within the buffer inlet line 181 by operating the buffer pump body 145. The buffer pump head 191 is configured to be operably arranged with the buffer pump body 145 in the cabinet 139 of the dilution skid 30 such that the buffer pump can be operated to pump at least one selected concentrated buffer solution from the concentrated buffer rack towers 22, 26, 27 through the buffer inlet line 181.

The WFI pump head 192 is disposed in the WFI inlet line 182 and is configured to be operably arranged with the WFI pump body 147 in the cabinet 139 of the inline dilution skid 30 to selectively generate a fluid displacement within the WFI inlet line 182 by operating the WFI pump body 147. The WFI pump head 192 is configured to be operably arranged with the WFI pump body 147 in the cabinet 139 of the dilution skid 30 such that the WFI pump can be operated to pump a supply of WFI from the WFI source through the WFI inlet line 182. In embodiments, the control unit 100 is configured to control at least one of a pump speed and a volume displacement of at least one of the buffer pump body 145 and the WFI pump body 147 to adjust a volumetric ratio of a buffer solution flowing through the buffer inlet line 181 and an amount of WFI flowing through the WFI inlet line 182 and being blended together in the discharge line 183.

In embodiments, the manifold 23 includes at least one buffer characteristic sensor 171, 173 disposed in the discharge line 183 that is configured to detect a value of a buffer characteristic of a fluid in the discharge line 183 and to generate a buffer characteristic signal indicative of the sensed value for the buffer characteristic. In the illustrated embodiment, the manifold 23 includes two buffer characteristic sensors 171, 173 disposed in the discharge line 183, namely, a conductivity sensor 171 and a pH sensor 173, that are respectively configured to transmit a conductivity signal and a pH signal to the control unit 100.

In embodiments, at least one operational sensor 172 can also be provided in the discharge line 183. The control unit 100 can be configured to use the signal received from the operational sensor 172 to determine whether the manifold 23 is operating within a desired operational range for a desired fluid characteristic. In the illustrated embodiment, the manifold 23 includes a pressure sensor 172 disposed in the discharge line 183 that is configured to transmit a pressure signal to the control unit 100. The control unit 100 can be configured to use the pressure signal to determine whether the manifold 23 is operating within a desired operational pressure range, such as within a safe operating pressure range, for example.

In embodiments, and as illustrated in FIG. 7, at least one buffer characteristic sensor 174 is associated with the waste line 184 and is configured to sense a value of a buffer characteristic of a buffer solution in the waste line 184 and to transmit a buffer characteristic signal indicative of the sensed value for the buffer characteristic to the control unit 100. In embodiments, the control unit 100 can use the received buffer characteristic signal from the waste line 184 to control the operation of the buffer management system 20.

In embodiments, the buffer characteristic sensor 174 in the waste line 184 can be any suitable sensor, for example, a conductivity sensor. In embodiments, the discharge line 183 and the waste line 184 can have associated therewith at least one sensor 171, 174 of the same type. For example, in embodiments, the first buffer characteristic sensor 171 in the discharge line 183 and the buffer characteristic sensor 174 in the waste line 184 both comprise a conductivity sensor.

In the illustrated embodiment, the second conductivity sensor 174 disposed in the waste line 184 is configured to transmit a second conductivity signal to the control unit 100. In embodiments, the buffer management program can be configured to use the second conductivity signal to identify the liquid passing through the waste line 184 and/or to determine whether the buffer solution passing through the waste line 184 is within a predetermined tolerance range of a given specification for a desired buffer. In embodiments, the control unit 100 is configured to assess, using the second conductivity signal from the second conductivity sensor 174, whether the conductivity of the WFI is within a predetermined range such that it is suitable for use in preparing desired buffer solutions. In embodiments, the control unit 100 is configured to determine whether the liquid passing through the waste line is within a predetermined tolerance range of a given specification for a desired buffer based upon the buffer characteristic signal and to occlude the waste line 184 via the third waste control valve 167 (and to open one of the buffer discharge ports 211-216) when the fluid in the waste line is within the predetermined tolerance range.

In embodiments, the control unit 100 is configured to automatically control the operation of the buffer management system 20 to prepare a buffer solution within a predetermined tolerance of a given specification. In embodiments, the control unit 100 is configured to automatically control the operation of at least one of the buffer pump and the WFI pump in response to information received via at least one sensor feedback loop to produce a desired buffer solution. In embodiments, the control unit 100 is configured to control the pump speed/volume displacement of at least one of the buffer pump and the WFI pump to adjust the ratio of the concentrated buffer to the WFI being blended together in the discharge line 183 to achieve a desired buffer recipe.

Referring to FIG. 7, in embodiments, the processor 107 is programmed with the buffer management program which is stored on the computer readable medium 108. In embodiments, the buffer management program includes an identification module configured to identify automatically buffer solutions passing through the manifold 23. In embodiments, the identification module is configured to identify automatically the concentrated buffer solution entering the manifold 23 via one of the buffer inlet ports 201-206 and passing through the manifold 23 based upon at least one buffer characteristic signal transmitted from at least one buffer characteristic sensor 171, 173, 174. In the illustrated embodiment, the processor 107 is in electrical communication with each of the buffer characteristic sensors 171, 173, 174 of the manifold 23 to receive a respective buffer characteristic signal therefrom.

In embodiments, the data storage device 109 includes buffer solution characteristic data for a plurality of different buffer recipes. The identification module of the buffer management program can be configured to identify the concentrated buffer solution passing through the manifold 23 by analyzing at least one buffer characteristic signal received from at least one buffer characteristic sensor 171, 173, 174 to determine which one of the buffer recipes most closely matches the buffer characteristic signal(s) received from the buffer characteristic sensor(s) 171, 173, 174.

In embodiments, the buffer recipes stored in the data storage device 109 each includes buffer solution characteristic data for at least two different buffer characteristics (such as, e.g., conductivity and pH). In embodiments, the identification module of the buffer management program is configured to identify the concentrated buffer solution passing through the manifold based upon the values of buffer characteristic signals from two different buffer characteristic sensors 171-74, such as, the pH sensor 173 and at least one of the buffer conductivity sensors 171, 174.

In embodiments, the buffer recipes can be loaded onto the storage device 109 using any suitable technique as will be appreciated by one skilled in the art. For example, in embodiments, the control unit 100 includes a human machine interface (HMI) 110 which is configured to receive operator input in the form of at least one buffer recipe. In embodiments, the buffer management program includes a recipe manager module configured to store buffer solution characteristic date for at least one buffer recipe in the data storage device for use by the identification module. The recipe manager module can be configured to store in a logical manner for use by the processor 107 at least one buffer recipe entered into the storage device 109 via the HMI 110.

In embodiments, the identification module of the buffer management program is configured to sequentially draw concentrated buffer solution through each one of the buffer inlet ports 201-06 to identify which one of the set of concentrated buffer solutions from the concentrated buffer rack towers 22, 26, 27 is connected to which one of the buffer inlet ports 201-206 based upon the buffer characteristic signal(s) received form the buffer characteristic sensor(s) 171, 173, 174. The identification module of the buffer management program can be configured to store in the data storage device 109 the identity of the concentrated buffer solution fluidly connected to each one of the buffer inlet ports 201-206.

Embodiments of a buffer management system 20 constructed in accordance with principles of the present disclosure can reduce the space required in buffer preparation rooms relative to conventional approaches. In applications using a relatively large quantity of full strength buffer needed to be produced, for instance 2,000 L, only a 200 L tote (based on 10× dilution) can be used. In applications with a total volume of buffer for a campaign of 20,000 L, a 2,000 L of concentrated buffer solution (based on 10× dilution) can be used with a buffer management system constructed according to principles of the present disclosure.

In other embodiments of a buffer management system constructed in accordance with principles of the present disclosure, the inline buffer dilution system construction can take alternatives forms. For example, in embodiments, the workstations can be replaced by totes. In other embodiments, the buffer management system can be scaled for larger buffer volumes or decreased for laboratory usage. In embodiments, a manifold assembly can be constructed from rigid plastic construction. In embodiments, a management system constructed according to principles of the present disclosure can be used to process liquids other than buffer solutions to meet the requirements of another application.

In embodiments of a method of using a buffer management system 20 following principles of the present disclosure, a buffer management system 20 constructed according to principles of the present disclosure is used to produce a desired buffer solution on a continuous basis as discussed herein. In embodiments, a method of using a buffer management system following principles of the present disclosure can be used with any embodiment of a buffer management system 20 according to principles discussed herein, which can include an embodiment of an inline dilution skid 30 having a single use manifold 23 according to principles of the present disclosure.

In one embodiment, a method of using a buffer management system 20 includes drawing an amount of buffer concentrate and an amount of water for injection (WFI) to an inline dilution skid 30. The amount of buffer concentrate and the amount of WFI are mixed at the inline dilution skid to form a diluted buffer solution.

A buffer characteristic of the diluted buffer solution is sensed at the inline dilution skid 30. A buffer characteristic signal indicative of a value for the sensed buffer characteristic is transmitted to a control unit 100. The control unit 100 is used to determine whether the diluted buffer solution is within a predetermined tolerance range for a selected buffer recipe based upon the buffer characteristic signal. The diluted buffer solution is discharged from the inline dilution skid 30 to a biocontainer 55 once the control unit determines the diluted buffer solution is within the predetermined tolerance range.

In embodiments, the method further includes discharging the diluted buffer solution from the inline dilution skid 30 through a waste line 184 when the control unit 100 determines the diluted buffer solution is outside of the predetermined tolerance range. The controller 100 is used to adjust at least one of a buffer pump drawing the amount of buffer concentrate to the inline dilution skid and a WFI pump drawing the amount of WFI to the inline dilution skid 30 based upon the buffer characteristic signal.

In embodiments, an embodiment of a buffer management system 20 constructed according to principles of the present disclosure can be used to draw at least one buffer concentrate stored in the concentrated buffer rack towers 22, 26, 27 through tubing to the inline dilution skid 30 and to mix the concentrated buffer with an amount of WFI (water for injection) in a ratio that is variable by adjusting at least one of the buffer pump and the WFI pump through the mixing T-piece 185. Once mixed, the diluted buffer solution passes through the first conductivity sensor 171 and then the pH sensor 173. The buffer management program of the control unit 100 can be operated to determine whether the diluted buffer solution passing through the discharge line 183 is within a predetermined tolerance for a selected buffer recipe based upon at least one of the first conductivity signal and the pH signal. The diluted buffer solution is diverted to the waste line 184 until the correct specification is reached. The control unit 100 is configured to automatically control the manifold 23 to produce the desired diluted buffer recipe and to send the diluted buffer solution to the desired surge container bag 55 of the diluted buffer rack towers 28, 29 through the control of the control valves 201-217 of the dilution skid 30 and the control of at least one of the buffer pump and the WFI pump based upon the signals received from the feedback sensors 171, 173, 174.

The second conductivity signal from the second conductivity sensor 174 in the waste line 184 can be sent to the control unit 100 and used by the buffer management program to determine whether the diluted buffer solution passing through the waste line 184 is within the specification for the selected buffer recipe. Because mixing of the concentrated buffer solution and the WFI can continue as the combined liquids pass through the waste line 184, it can be helpful to monitor the second conductivity signal to determine whether the diluted buffer solution is within the specification for the desired recipe to reduce the amount of solution diverted to the waste line 184.

Once the control unit 100 determines that the diluted buffer solution being produced within the manifold 23 is within the specification for the desired buffer recipe, the control unit 100 can operate the manifold 23 so that the diluted buffer solution is directed to a selected one of the surge biocontainers of the diluted buffer rack towers 28, 29. The diluted buffer solution stored in the selected surge biocontainer is ready to be sent to a process of operation (such as, TFF or chromatography, for example).

In embodiments of a method of using a buffer management system 20 following principles of the present disclosure, a buffer management system 20 constructed according to principles of the present disclosure is used to automatically identify the arrangement of buffer solutions in a bioprocessing application. In embodiments, a method of using a buffer management system to conduct buffer identification operations following principles of the present disclosure can be used with any embodiment of a buffer management system 20 according to principles discussed herein, which can include an embodiment of an inline dilution skid 30 having a single use manifold 23 according to principles of the present disclosure.

In one embodiment, a method of using a buffer management system includes drawing an amount of one of a set of concentrated buffer solutions into a first buffer inlet port of a plurality of buffer inlet ports of a manifold. A buffer characteristic of the concentrated buffer solution is sensed in the manifold. A buffer characteristic signal indicative of a value for the sensed buffer characteristic is transmitted to a control unit. The control unit is used to identify the concentrated buffer solution entering the manifold via the first buffer inlet port based upon the buffer characteristic signal.

In embodiments, buffer solution characteristic data for a plurality of buffer recipes can be loaded in a data storage device. The control unit can be configured to identify the concentrated buffer solution passing through the manifold by analyzing the buffer characteristic signal to determine one of the buffer recipes in the storage device that most closely matches the buffer characteristic signal. In at least some of such embodiments, a second buffer characteristic of the concentrated buffer solution, which is different form the first buffer characteristic, can be sensed in the manifold. A second buffer characteristic signal indicative of a value for the sensed second buffer characteristic can be transmitted to the control unit. The control unit can be configured to identify the concentrated buffer solution entering the manifold via the first buffer inlet port based upon the first buffer characteristic signal and the second buffer characteristic signal. In at least some of those embodiments, the first buffer characteristic and the second buffer characteristic respectively comprise conductivity and pH.

Embodiments of a method of using a buffer management system following principles of the present disclosure can include sequentially drawing an amount of a respective one of a set of concentrated buffer solutions into each one of a plurality of buffer inlet ports of the manifold. The buffer characteristic of the respective one of the set of concentrated buffer solutions can be sequentially sensed in the manifold. The buffer characteristic signal indicative of the value for the sensed buffer characteristic of the respective one of the set of concentrated buffer solutions can be sequentially transmitted to the control unit. The control unit can be sequentially used to identify the respective one of the set of concentrated buffer solutions entering the manifold via each one of the plurality of buffer inlet ports of the manifold based upon the buffer characteristic signal. The identity of the concentrated buffer solution fluidly connected to each one of the buffer inlet ports can be stored in the data storage device.

Embodiments of a method of using a buffer management system following principles of the present disclosure can include discharging an amount of liquid from a first buffer discharge port of a plurality of buffer discharge ports of the manifold into one of a plurality of biocontainers. The plurality of buffer discharge ports are in respective fluid communication with a different one of the plurality of biocontainers. An amount of material stored within each one of the plurality of biocontainers can be respectively sensed. A fill level signal indicative of a value for the amount of material sensed within each one of the plurality of biocontainers can be respectively transmitted to the control unit. The control unit is used to identify the biocontainer with which the first buffer discharge port is in fluid communication based upon the change of the fill level signal therefrom.

In embodiments, fluid is sequentially discharged through each one of the buffer discharge ports. The control unit is correspondingly sequentially used to identify the biocontainer with which each one of the buffer discharge ports is in fluid communication based upon the change of the fill level signal therefrom. The identity of the biocontainer fluidly connected to each one of the buffer discharge ports is stored in the data storage device.

Embodiments of a method of using a buffer management system following principles of the present disclosure can include sequentially discharging an amount of liquid from each one of the biocontainers into a respective one of a plurality of unit inlet ports of a bioprocessing unit. The plurality of biocontainers are in respective fluid communication with a different one of the unit inlet ports of the bioprocessing unit. The control unit is correspondingly sequentially used to identify the biocontainer with which each one of the unit inlet ports is in fluid communication based upon the change of the fill level signal therefrom.

Referring to FIGS. 8-11, a first biocontainer surge bag filling sequence is shown. In embodiments, each surge bag filling sequence includes flushing the manifold 23, diverting the buffer solution to the waste line 184 until the control unit 100 determines the buffer solution being produced is within a predetermined tolerance of a given diluted buffer recipe, and filling a selected one of the biocontainer surge bags of the diluted buffer rack towers 28, 29 to a predetermined volume. In the illustrated embodiment, the initial surge bag filling sequence includes flushing the manifold 23, priming the flow of WFI through the manifold 23, diverting the buffer solution to the waste line 184 until the control unit 100 determines the buffer solution being produced is within a predetermined tolerance of a given diluted buffer recipe, and filling a selected one of the biocontainer surge bags of the diluted buffer rack towers 28, 29 to a predetermined volume.

Figure 8:
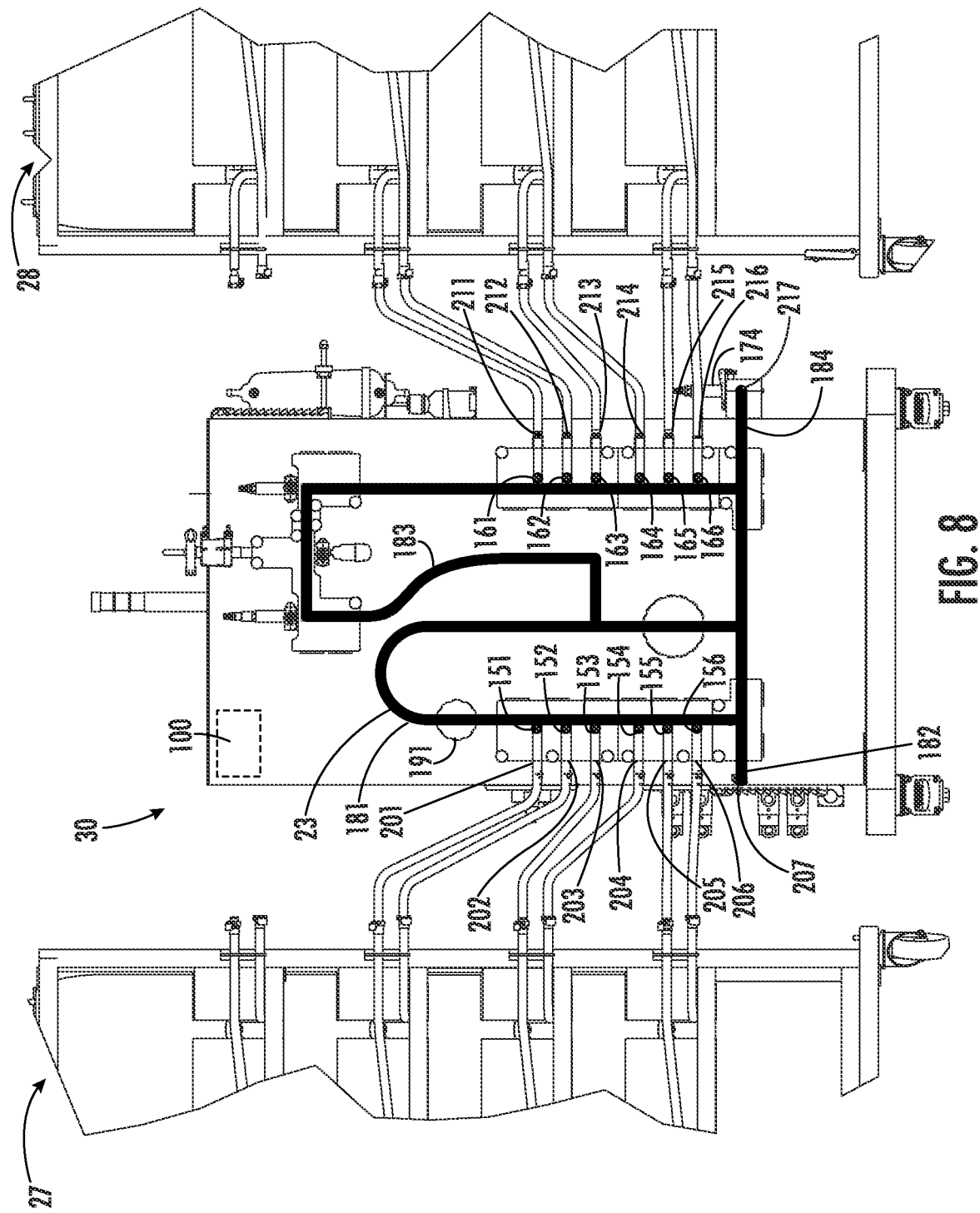
FIG. 8 is a fragmentary, elevational view of an embodiment of a buffer management system constructed in accordance with principles of the present disclosure that includes an embodiment of an inline dilution skid constructed according to principles of the present disclosure interposed between a concentrated buffer rack tower and a diluted buffer rack tower, illustrating the manifold in a flushing position.

Referring to FIG. 8, the manifold 23 is in a flushing position. The flushing step is performed to remove any traces of buffer solution or any other impurities in the manifold 23 to initiate each filling sequence. In the flushing position, the control unit 100 of the dilution skid 30 has controlled the control valves 151-167 such that the concentrated buffers of the concentrated buffer rack towers and the biocontainer assemblies of the diluted buffer rack towers 22, 26, 27 are all in fluid isolation from the manifold 23. The buffer inlet line 181, the WFI inlet line 182, the discharge line 183, and the waste line 184 are all in fluid communication with the WFI source via the WFI inlet port 207 such that WFI can flow through these lines 181, 182, 183, 184 and out the waste outlet port 217. In such an arrangement, when the manifold 23 is in the flushing position, there are established multiple flow paths through the manifold from the WFI inlet port 207 to the waste outlet port 217. In the illustrated embodiment, the control unit 100 has operated the buffer inlet control valves 151-156 and the buffer discharge control valves 161-66 to occlude the respective buffer inlet ports 201-206 and discharge ports 211-216.

In embodiments, the flushing step can be performed for a predetermined period of time. In embodiments, the flushing step can be performed until the buffer management program of the control unit 100 determines that the second conductivity signal from the second conductivity sensor 174 meets a predetermined specification.

Figure 9:
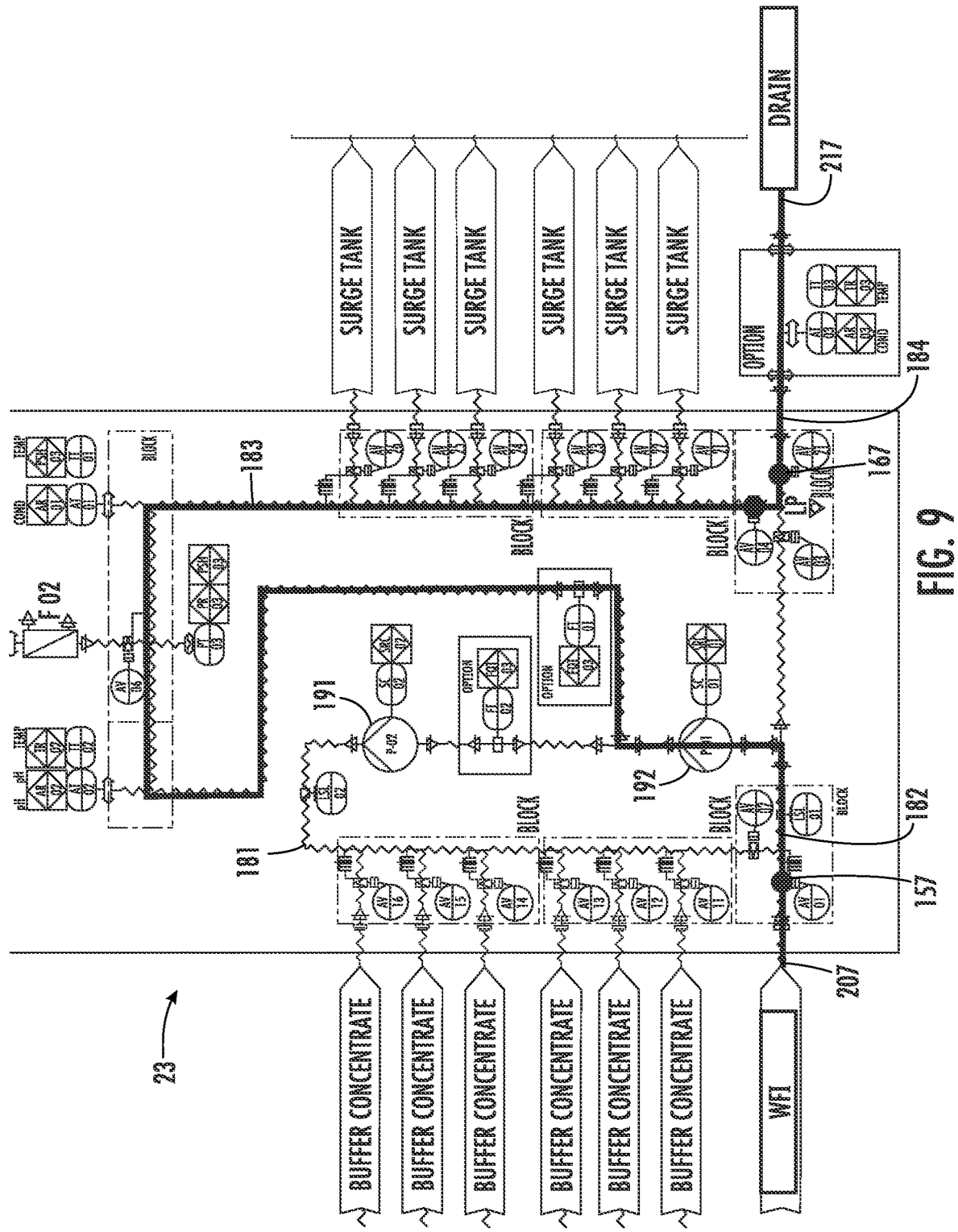
FIG. 9 is a fragmentary schematic view of a hydraulic circuit of the buffer management system of FIG. 8, illustrating the manifold in a water for injection (WFI) priming position.

Referring to FIG. 9, the manifold 23 is in a WFI priming position. Inasmuch as the demand for WFI in a typical buffer recipe can be in a range between five times and twenty times the amount of concentrated buffer solution being mixed with the WFI, the WFI pump 192 is larger than the buffer pump 191 in embodiments of the manifold. Proportionally the WFI is pumped at a greater volume than the buffer concentrate(s). The priming step can be included in order to bring the flow of WFI through the manifold 23 up to a steady state before introducing the desired concentrated buffer solution into the manifold 23 for mixing with the WFI.

In the WFI priming position, the control unit 100 of the dilution skid has controlled the control valves such that the concentrated buffers of the concentrated buffer rack towers and the biocontainer assemblies of the diluted buffer rack towers are all in fluid isolation from the manifold. The buffer inlet line 181 is in fluid isolation from the WFI inlet line 182, the discharge line 183, and the waste line 184. The WFI inlet 182, the discharge line 183, and the waste line 184 are all in fluid communication with the WFI source such that the WFI can flow into the WFI inlet port 207 through these lines 182, 183, 184 and out the waste outlet port 217. The control unit 100 has operate to open the WFI inlet control valve 157 and the third waste control valve 167. In such an arrangement, when the manifold 23 is in the priming position, there is established a flow path through the manifold 23 from the WFI inlet port 207 to the waste outlet port 217 via the WFI inlet line 182, the discharge line 183, and the waste line 184.

Figure 10:
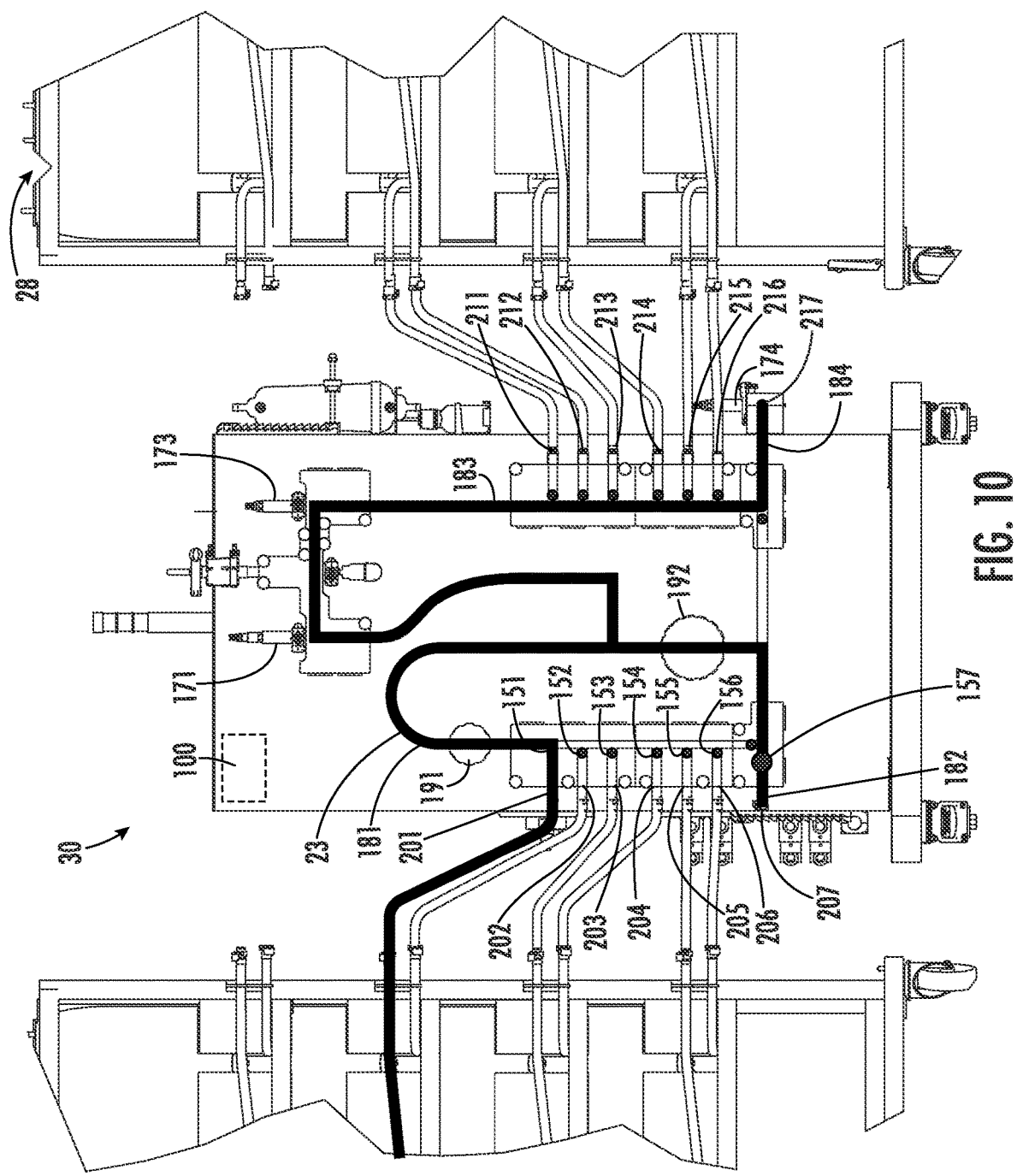
FIG. 10 is a view as in FIG. 8 of the buffer management system, illustrating the manifold in a first buffer stabilizing position.

Referring to FIG. 10, the manifold 23 is in a first buffer stabilizing position. The manifold 23 is maintained in the first buffer stabilizing position so that the diluted buffer solution that is initially produced is diverted to the waste line 184 until the control unit 100 determines the buffer solution being produced is within a predetermined tolerance of a given diluted first buffer recipe.

In the first buffer stabilizing position, the control unit 100 of the dilution skid has controlled the control valves 151-156 such that the first buffer inlet port 201 is in fluid communication with the buffer inlet line 181, and the other five buffer inlet ports 202-206 are in fluid isolation from the manifold 23. The control unit 100 has opened the WFI inlet control valve 157 such that the WFI inlet port is in fluid communication with the WFI inlet line 182 to allow a flow of WFI to enter therein. The buffer discharge ports 211-216 are in fluid isolation from the discharge line 183 such that biocontainer assemblies of the diluted buffer rack towers 28, 29 are all in fluid isolation from the manifold 23. The WFI inlet line 182 and the buffer inlet line 181 are in fluid communication with the discharge line 183, which in turn is in fluid communication with the waste line 184 such that the combined first buffer concentrate and the WFI that are flowing respectively through the buffer inlet line 181 and the WFI inlet line 182 can flow through the discharge line 183 and the waste line 184 out the waste outlet port 217. In such an arrangement, when the manifold 23 is in the first buffer stabilizing position, there are established multiple flow paths through the manifold 23, namely one flow path from the WFI inlet port 207 to the waste outlet port 217 and another flow path from the first buffer inlet port 201 to the waste outlet port 217.

In embodiments, the manifold 23 is maintained in the first buffer stabilizing position until the control unit 100 determines that the diluted buffer solution being produced in the manifold 23 is within a predetermined specification for the first buffer recipe. The control unit 100 can use the buffer data signals generated by at least one of the first conductivity sensor 171, the pH sensor 173, and the second conductivity sensor 174 to determine whether the diluted buffer solution being produced in the manifold 23 is within the specification for the desired first buffer recipe. In embodiments, the control unit 100 can be configured to adjust at least one of the buffer pump 191 flow rate and the WFI pump 192 flow rate to adjust the ratio of buffer concentrate and WFI being blended together in the manifold 23 when the diluted buffer solution being produced in the manifold 23 is not within the specification for the first diluted buffer recipe. The control unit 100 can be configured to use the sensor feedback loop(s) to adjust the operation of the buffer management system 20 until it is determined that the diluted buffer solution being produced in the manifold 23 is within the specification for the desired first buffer recipe.

In the first buffer stabilizing position, the diluted buffer solution that is sent through the waste line 184 passes through the second conductivity sensor 174 positioned near the waste outlet port 217. Because the combined flows of the first buffer concentrate and the WFI continue to mix in the discharge line 183 between the first conductivity sensor 171 and the second conductivity sensor 174, the second conductivity signal can be used to help more quickly detect when the diluted buffer solution has achieved the specification of the desired first diluted buffer recipe so as to reduce the amount of viable buffer solution that is sent to waste.

Figure 11:
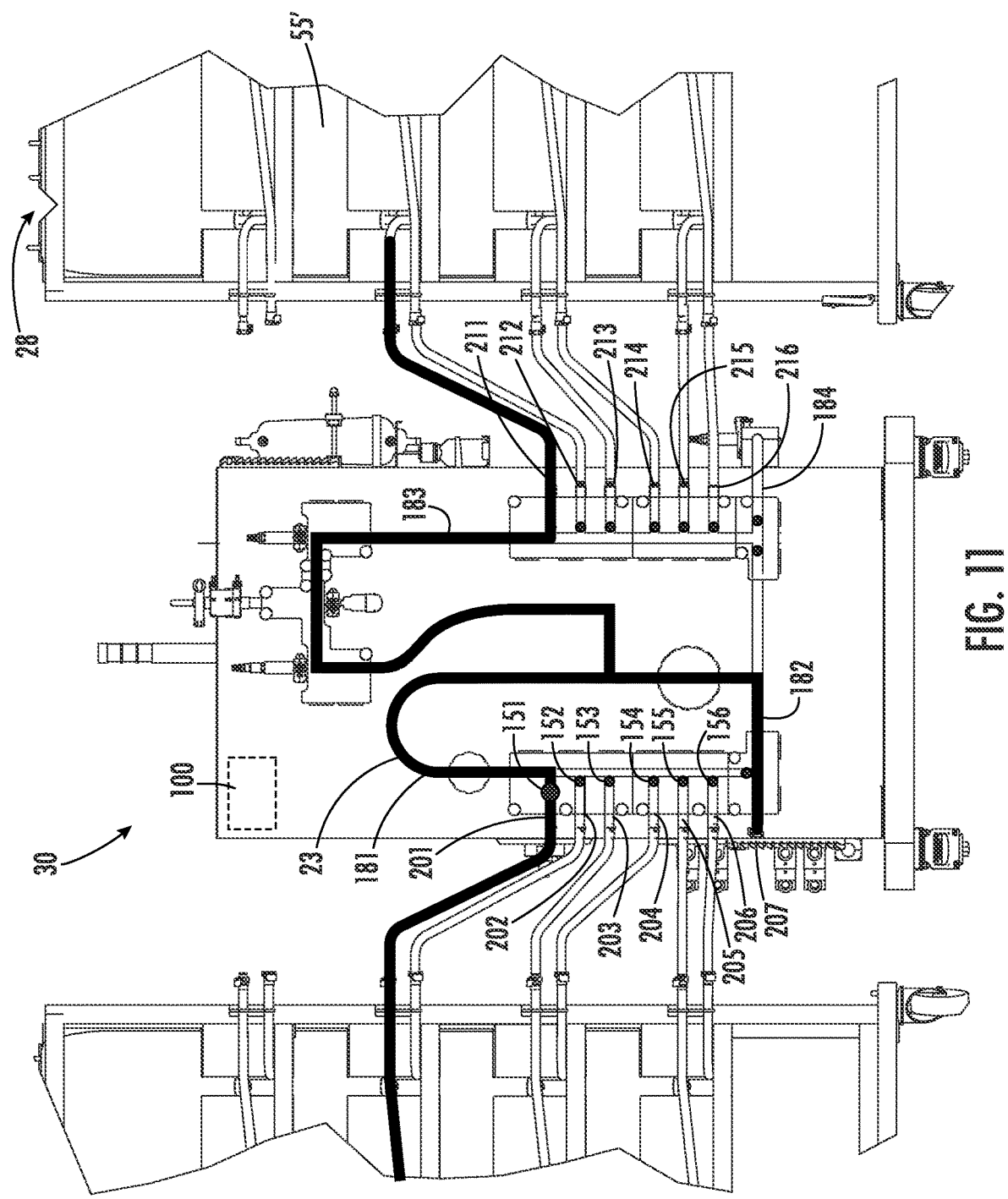
FIG. 11 is a view as in FIG. 8 of the buffer management system, illustrating the manifold in a first buffer filling position.

Referring to FIG. 11, the manifold 23 is in a first buffer filling position. The manifold 23 is maintained in the first buffer filling position so that the diluted buffer solution that is within the specification for the desired first diluted buffer recipe is conveyed to the designated surge bag 55' of the diluted buffer rack towers 28, 29 for the first diluted buffer recipe.

In the first buffer filling position, the control unit 100 of the dilution skid 30 has controlled the control valves 151-56 such that the first buffer inlet port 201 is in fluid communication with the buffer inlet line 181, and the other five buffer inlet ports 202-206 are in fluid isolation from the manifold 23. The first buffer discharge port 211 is in fluid communication with the discharge line 183 of the manifold 23, and the other buffer discharge ports 212-216 are in fluid isolation from the manifold 23. The first buffer discharge port 211 is in fluid communication with the biocontainer bag 55' of the first diluted buffer rack tower 28 designated for receiving buffer solution made according to the first diluted buffer recipe. The buffer inlet line 181 and the WFI inlet line 182 are in fluid communication with the discharge line 183, which in turn is in fluid communication with the first buffer discharge port 211 such that the combined first buffer concentrate and the WFI that are flowing respectively through the buffer inlet line 181 and the WFI inlet line 182 can flow through the discharge line 183 and out the first buffer discharge port 211. The waste line 184 is in fluid isolation from the discharge line 183. In such an arrangement, when the manifold 23 is in the first buffer filling position, there are established multiple flow paths through the manifold 23, namely one flow path from the WFI inlet port 207 to the first buffer discharge port 211 and another flow path from the first buffer inlet port 201 to the first buffer discharge port 211 such that the first buffer discharge port 211 receives diluted buffer solution blended according to a first diluted buffer recipe.

In the illustrated embodiment, in the first buffer filling position, the first buffer discharge port 211 is in fluid communication with the biocontainer bag 55' of the diluted buffer rack towers designated for receiving buffer solution made according to the first diluted buffer recipe via the first buffer discharge port 211. It will be understood that in other embodiments, another buffer discharge port (such as the third buffer discharge port 213, for example) can be fluidly connected to the designated biocontainer bag for receiving the first diluted buffer recipe. In such an arrangement, when the manifold is in the first buffer filling position, there is established through the manifold a flow path from the first buffer inlet port to the third buffer discharge port.

The manifold 23 can be maintained in the first buffer filling position to fill the designated surge bag 55' with the first diluted buffer solution until the control unit 100 of the dilution skid 30 receives a first fill level signal from the first diluted buffer rack tower 28 that indicates the designated surge bag 55' has stored within it a predetermined maximum fill amount of the first buffer solution. Once the control unit 100 has received the fill level signal indicating that the designated surge bag 55' has a desired maximum amount of the first buffer solution, the control unit 100 can be operated to discontinue the production of the first buffer solution.

In embodiments, the control unit 100 can be configured to maintain the volume of first buffer solution in the surge bag 55' to a desired minimum fill level. In embodiments, when the first fill level signal from the first biocontainer bag 55' indicates that the level of first buffer solution in the first biocontainer bag 55' is below a predetermined level, the control unit 100 can be configured to run the first buffer filling sequence to bring the level of first buffer solution back above a predetermined operating level. In embodiments, the operating level can be different from the maximum fill level. In embodiments, each biocontainer assembly can be configured to monitor the level of liquid within each biocontainer bag 55 as part of a bioprocessing application. In embodiments, the buffer management system 20 can be configured to use the fill level signal received from each capacitive liquid level sensor of the biocontainer assemblies to monitor how volume of liquid stored within each bag 55 changes and thus gain real time feedback. The monitoring of the fill level signals can be used in the buffer management system 20 for various modes of operation. For example, in embodiments, the fill level signals can be monitored to maintain the volume of buffer solution in each respective surge bag 55' to a desired minimum fill level.

Figure 12:
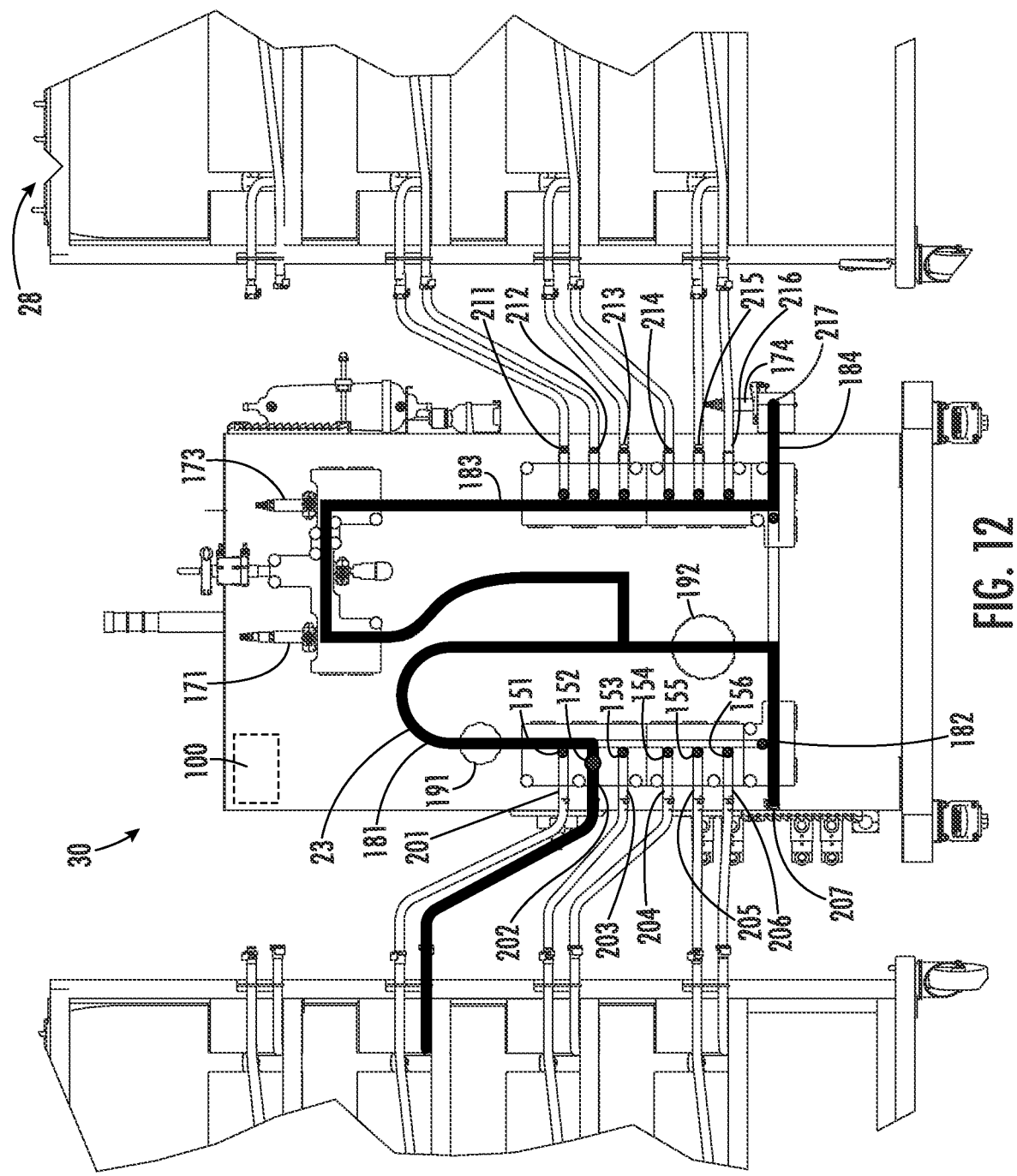
FIG. 12 is a view as in FIG. 8 of the buffer management system, illustrating the manifold in a second buffer stabilizing position.
Figure 13:
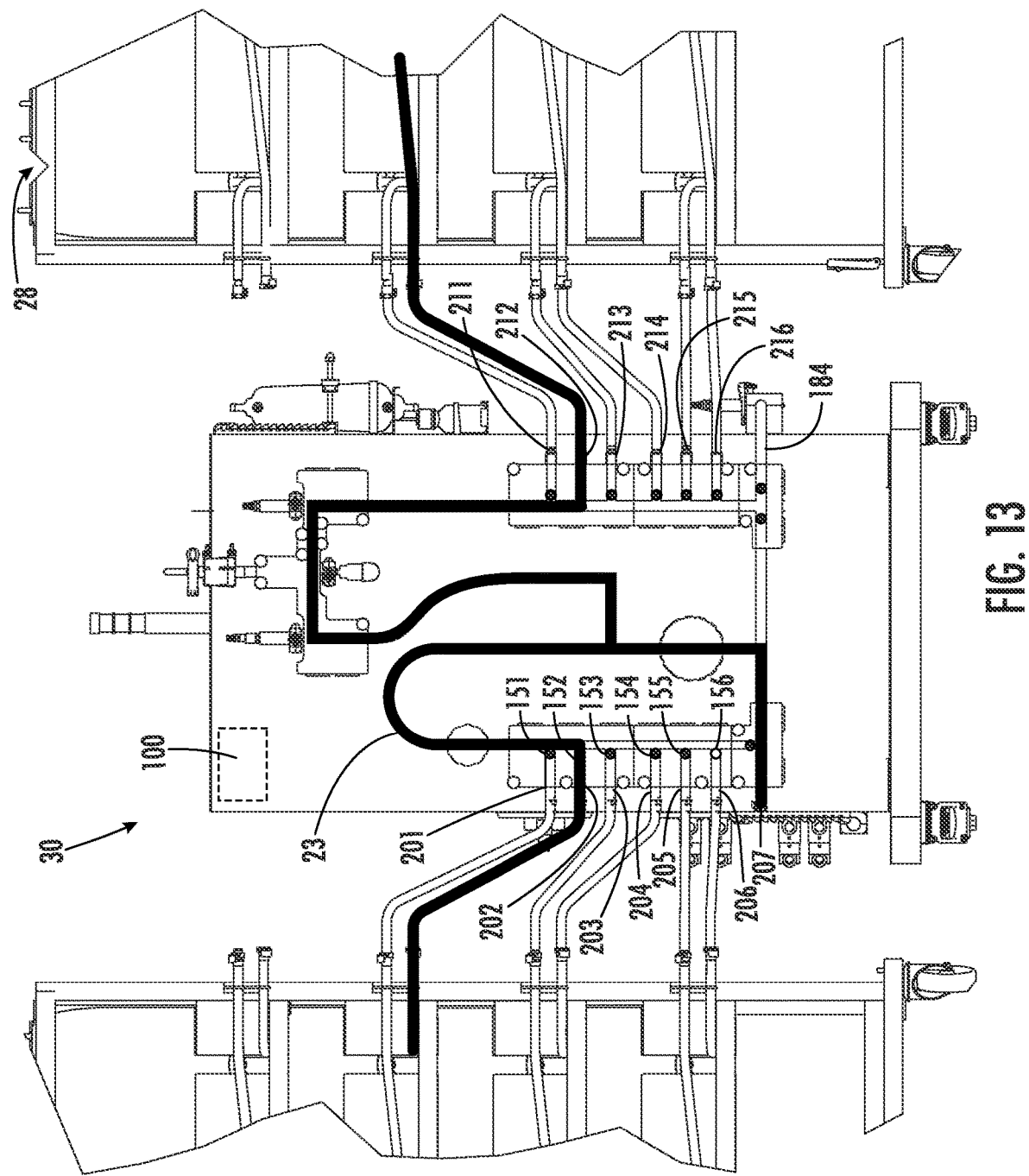
FIG. 13 is a view as in FIG. 8 of the buffer management system, illustrating the manifold in a second buffer filling position.

Referring to FIGS. 12 and 13, a second biocontainer surge bag filling sequence is shown. In embodiments, different buffer solutions are used for a given bioprocessing application. In embodiments, the buffer management system 20 is configured to produce different diluted buffer solution recipes for use in such bioprocessing applications. In embodiments, the buffer management system 20 can be used to produce multiple diluted buffer solutions in sequence. The dilution skid 30 can be configured to conduct a flushing step each time it switches production of diluted buffer solution from one buffer recipe to a different buffer recipe. In embodiments, the buffer management system 20 begins each filling sequence with a flushing cycle as is shown in FIG. 8. In embodiments, the second surge bag filling sequence includes flushing the manifold 23, diverting the second buffer solution to the waste line 184 until the control unit 100 determines the buffer solution being produced is within a predetermined tolerance of a given second diluted buffer recipe, and filling a selected one of the biocontainer surge bags of the diluted buffer rack towers 28, 29 to a predetermined volume.

In embodiments, priming is included in the initial buffer filling sequence when the system 20 draws in any liquid in the manifold 23 (which is dry until this point) for the first time. When the system 20 switches between buffers, i.e. dilutes one buffer and ready to move on to the second buffer, WFI flushing alone can be sufficient between these two steps (no priming needed as the manifold is already full of liquid from the previous step).

Referring to FIG. 12, the manifold 23 is in a second buffer stabilizing position. The manifold 23 is maintained in the second buffer stabilizing position so that the diluted buffer solution that is initially produced is diverted to the waste line 184 until the control unit 100 determines the buffer solution being produced is within a predetermined tolerance of a given second diluted buffer recipe. In embodiments, the second diluted buffer recipe is different from the first diluted buffer recipe.

In the second buffer stabilizing position, the control unit 100 of the dilution skid 30 has controlled the control valves 151-156 such that the second buffer inlet port 202 is in fluid communication with the buffer inlet line 181, and the first and third through sixth buffer inlet ports 201, 203-206 are in fluid isolation from the manifold 23. The control unit 100 has opened the WFI inlet control valve 157 such that the WFI inlet port 207 is in fluid communication with the WFI inlet line 182 to allow a flow of WFI to enter therein. The buffer discharge ports 211-216 are in fluid isolation from the discharge line 183 such that biocontainer assemblies of the diluted buffer rack towers 28, 29 are all in fluid isolation from the manifold 23. The buffer inlet line 181 and the WFI inlet line 182 are in fluid communication with the discharge line 183, which in turn is in fluid communication with the waste line 184 such that the combined second buffer concentrate and the WFI that are flowing respectively through the buffer inlet line 181 and the WFI inlet line 182 can flow through the discharge line 183 and the waste line 184 out the waste outlet port 217. In such an arrangement, when the manifold 23 is in the second buffer stabilizing position, there are established multiple flow paths through the manifold 23, namely one flow path from the WFI inlet port 207 to the waste outlet port 217 and another flow path from the second buffer inlet port 202 to the waste outlet port 217.

In embodiments, the manifold 23 is maintained in the second buffer stabilizing position until the control unit 100 determines that the diluted buffer solution being produced in the manifold 23 is within a predetermined specification for the second buffer recipe. The control unit 100 can be configured to control the operation of the manifold 23 in a manner as described above in connection the with first buffer stabilizing position. The control unit 100 can use the buffer data signals generated by at least one of the first conductivity sensor 171, the pH sensor 173, and the second conductivity sensor 174 to determine whether the diluted buffer solution being produced in the manifold 23 is within the specification for the desired second diluted buffer recipe. In embodiments, the control unit 100 can be configured to adjust at least one of the buffer pump 191 flow rate and the WFI pump 192 flow rate to adjust the ratio of buffer concentrate and WFI being blended together in the manifold in response to determining that the diluted buffer solution being produced in the manifold 23 is not within the specification for the second diluted buffer recipe. The control unit 100 can use the sensor feedback loop(s) to adjust the operation of the buffer management system until it is determined that the diluted buffer solution being produced in the manifold 23 is within the specification for the desired second diluted buffer recipe.

Referring to FIG. 13, the manifold 23 is in a second buffer filling position. The manifold 23 is maintained in the second buffer filling position so that the diluted buffer solution that is within the specification for the desired second diluted buffer recipe is conveyed to the designated surge bag of the diluted buffer rack towers 28, 29 for the second diluted buffer recipe.

In the second buffer filling position, the control unit 100 of the dilution skid 30 has controlled the control valves 151-156 such that the second buffer inlet port 202 is in fluid communication with the buffer inlet line 181, and the first and third through sixth buffer inlet ports 201, 203-206 are in fluid isolation from the manifold 23. The second buffer discharge port 212 is in fluid communication with the discharge line of the manifold, and the first and third through sixth buffer discharge ports 211, 213-216 are in fluid isolation from the manifold 23. The second buffer discharge port 212 is in fluid communication with the biocontainer bag of the diluted buffer rack towers 28, 29 designated for receiving buffer solution made according to the second diluted buffer recipe. The buffer inlet line 181 and the WFI inlet line 182 are in fluid communication with the discharge line 183, which in turn is in fluid communication with the second buffer discharge port 212 such that the combined second buffer concentrate and the WFI that are flowing respectively through the buffer inlet line 181 and the WFI inlet line 182 can flow through the discharge line 183 and out the second buffer discharge port 212. The waste line 184 is in fluid isolation from the discharge line 183. In such an arrangement, when the manifold 23 is in the second buffer filling position, there are established multiple flow paths through the manifold, namely one flow path from the WFI inlet port 207 to the second buffer discharge port 212 and another flow path from the second buffer inlet port 202 to the second buffer discharge port 212 such that the second buffer discharge port 212 receives diluted buffer solution blended according to the second diluted buffer recipe.

In the illustrated embodiment, in the second buffer filling position, the second buffer discharge port 212 is in fluid communication with the biocontainer bag of the diluted buffer rack towers 28, 29 designated for receiving buffer solution made according to the second diluted buffer recipe via the second buffer discharge port 212. It will be understood that in other embodiments, another buffer discharge port (such as the third buffer discharge port 213, for example) can be fluidly connected to the designated biocontainer bag for receiving the second diluted buffer recipe. In such an arrangement, when the manifold 23 is in the second buffer filling position, there is established through the manifold a flow path from the second buffer inlet 202 port to the third buffer discharge port 213.

The manifold 23 can be maintained in the second buffer filling position to fill the designated surge bag with the second diluted buffer solution until the control unit 100 receives a second fill level signal from the diluted buffer rack towers 28, 29 that indicates the designated surge bag has stored within it a predetermined maximum fill amount of the second buffer solution. Once the control unit 100 has received the second fill level signal indicating that the designated surge bas has a desired maximum amount of the second buffer solution, the control unit 100 can be operated to discontinue the production of the second buffer solution. The operation of the dilution skid 30 with respect to the production and maintenance of the second diluted buffer solution can be similar in other respects to that described with respect to the first diluted buffer solution.

In the illustrated embodiment, the manifold 23 includes six buffer inlet ports 201-206 for a maximum of six different buffer concentrates for use in producing buffer solutions of different diluted buffer recipes. The buffer filling sequence can be performed in a similar manner for the third through sixth concentrated buffer solutions with the third through sixth buffer inlet ports 203-206, respectively. In other embodiments, a different number of buffer inlet ports 201-206 can be provided.

Figure 14:
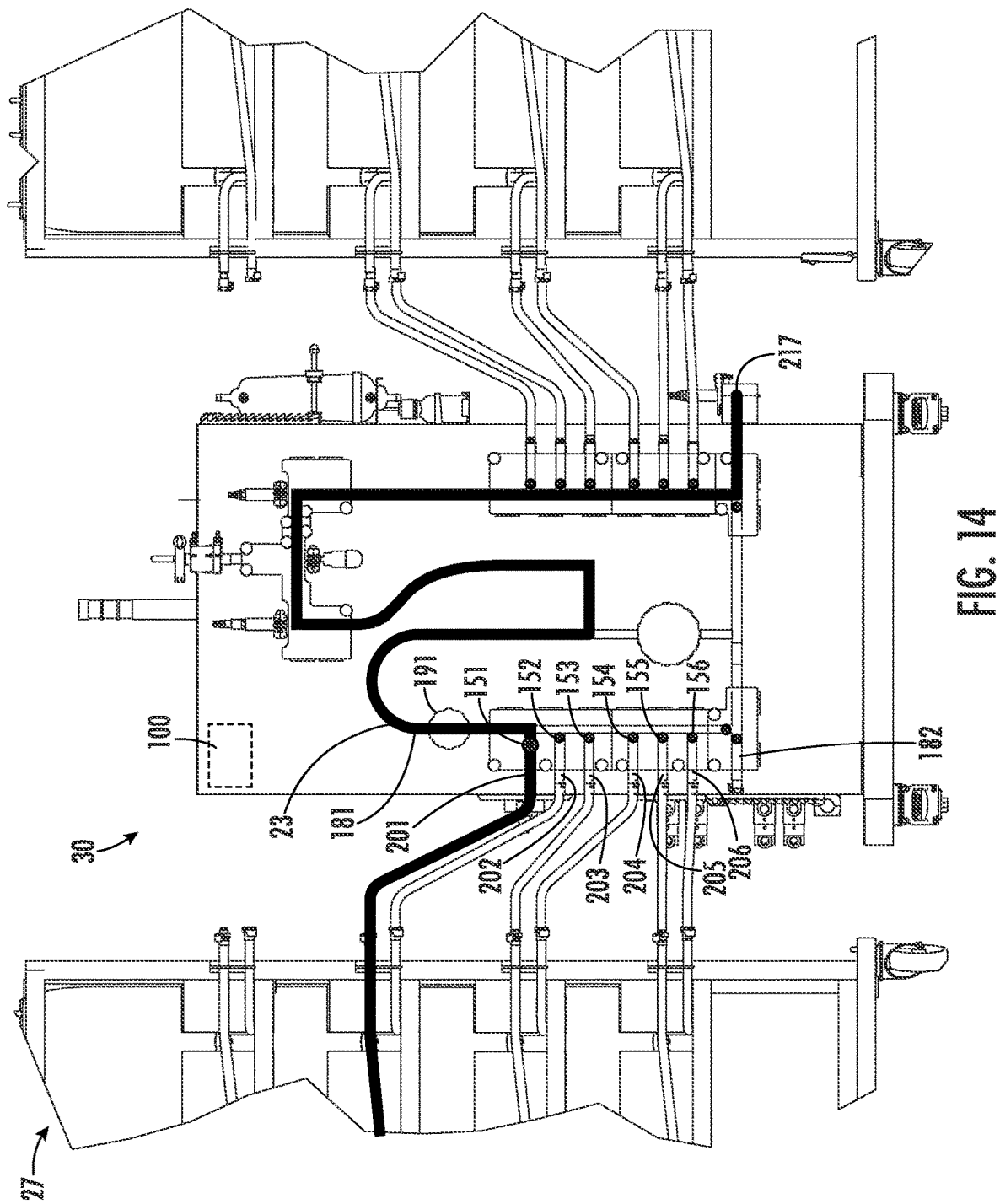
FIG. 14 is a view as in FIG. 8 of the buffer management system, illustrating the manifold in a first concentrated buffer draining position.
Figure 15:
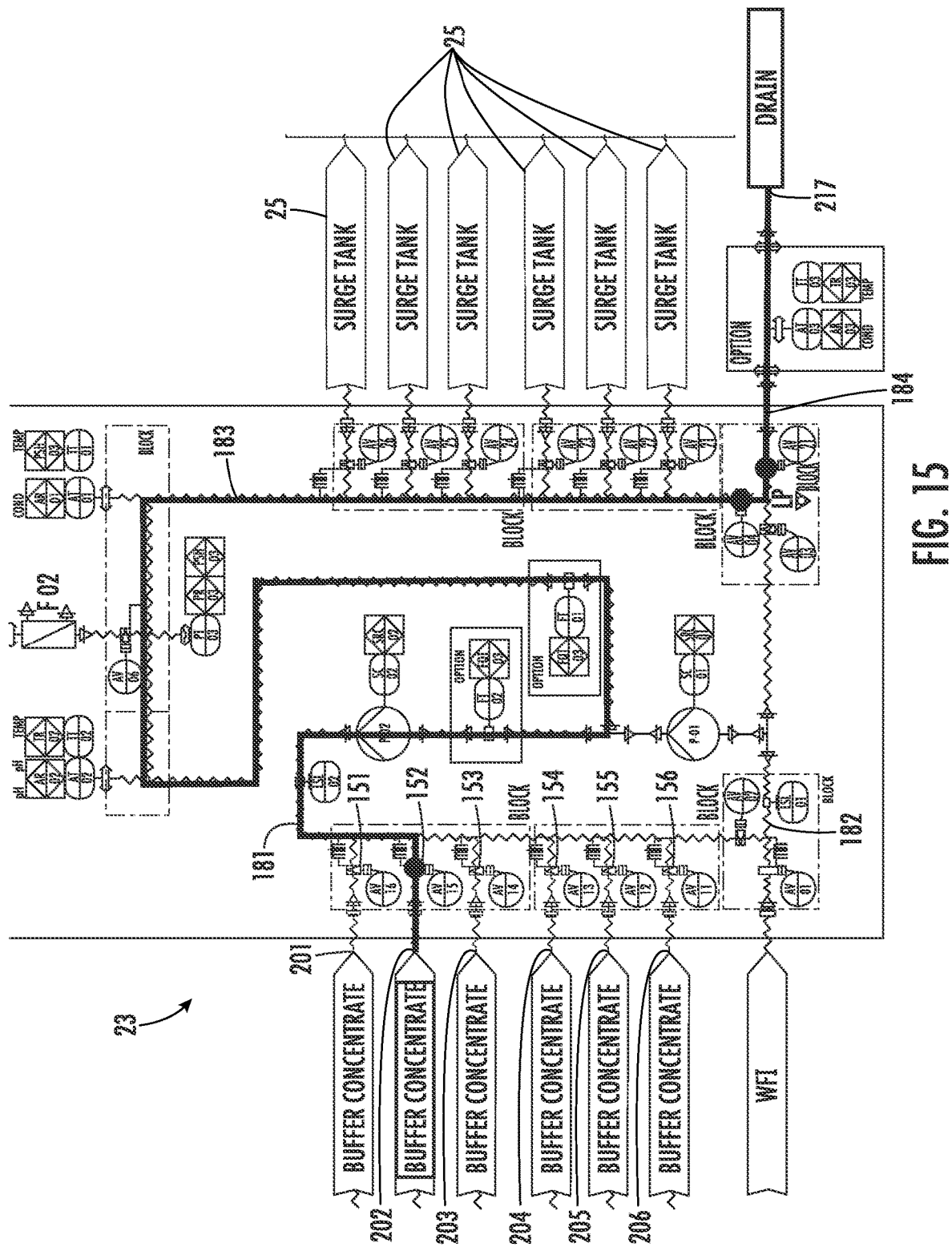
FIG. 15 is a view as in FIG. 9 of the hydraulic circuit of the buffer management system of FIG. 8, illustrating the manifold in a second concentrated buffer draining position.

Referring to FIGS. 14 and 15, a buffer concentrate draining sequence is shown. In embodiments, each buffer concentrate stored in the concentrated buffer rack towers 22, 26, 27 can be drained from the respective totes in a sequential manner. Such an operation can occur after the completion of the desired bioprocessing application to facilitate the preparation of the buffer management system 20 for another bioprocessing application using a new single use manifold.

Referring to FIG. 14, the manifold 23 is in a first concentrated buffer draining position. The manifold 23 is maintained in the first concentrated buffer draining position so that the first concentrated buffer solution stored in the concentrated buffer rack towers 22, 26, 27 can be drained therefrom.

In the first concentrated buffer draining position, the control unit 100 of the dilution skid 30 has controlled the control valves 151-156 such that the first buffer inlet port 201 is in fluid communication with the buffer inlet line 181, and the other five buffer inlet ports 202-06 are in fluid isolation from the manifold 23. The biocontainer assemblies of the diluted buffer rack towers 28, 29 are all in fluid isolation from the manifold 23. The buffer inlet line 181 is in fluid communication with the discharge line 183, which in turn is in fluid communication with the waste line 184 such that the first buffer concentrate can flow from the concentrated buffer rack towers 22, 26, 27 through the first buffer inlet port 201, the buffer inlet line 181, the discharge line 183, and the waste line 184 out through the waste outlet port 217. The WFI inlet line 182 is in fluid isolation from the buffer inlet line 181, the discharge line 183, and the waste line 184. In such an arrangement, when the manifold 23 is in the first concentrated buffer draining position, there is established a flow path from the first buffer inlet port 201 through the manifold 23 to the waste outlet port 217.

The control unit 100 can be configured to operate the buffer pump 191 to carry out a first concentrated buffer draining sequence. In embodiments, the control unit 100 can be configured to operate the first concentrated buffer draining sequence by placing the manifold 23 in the first concentrated buffer draining position and operating the buffer pump 191 for a predetermined period of time. In embodiments, the buffer management system can include a suitable flow meter along the drain path for the first concentrated buffer solution that is communicatively arranged with the control unit 100 to receive a flow signal therefrom indicative of the flow of liquid through the flow path. In embodiments, the control unit 100 can be configured to operate the buffer pump 191 to carry out the first concentrate buffer draining sequence until the flow signal indicates that the flow of liquid along the drain path is below a predetermined threshold.

Referring to FIG. 15, the manifold 23 is in a second concentrated buffer draining position. The manifold 23 is maintained in the second concentrated buffer draining position so that the second concentrated buffer solution stored in the concentrated buffer rack towers can be drained therefrom.

In the second concentrated buffer draining position, the control unit of the dilution skid has controlled the control valves 151-156 such that the second buffer inlet port 202 is in fluid communication with the buffer inlet line 181, and the first and third through sixth buffer inlet ports 201, 203-206 are in fluid isolation from the manifold 23. The biocontainer assemblies 25 of the diluted buffer rack towers are all in fluid isolation from the manifold 23. The buffer inlet line 181 is in fluid communication with the discharge line 183, which in turn is in fluid communication with the waste line 184 such that the second buffer concentrate can flow from the concentrated buffer rack towers through the second buffer inlet port 202, the buffer inlet line 181, the discharge line 183, and the waste line 184 out through the waste outlet port 217. The WFI inlet line 182 is in fluid isolation from the buffer inlet line 181, the discharge line 183, and the waste line 184. In such an arrangement, when the manifold 23 is in the second concentrated buffer draining position, there is established a flow path from the second buffer inlet port 202 through the manifold 23 to the waste outlet port 217.

The control unit can be configured to carry out a second concentrated buffer draining sequence in a manner similar to that described above in connection with the first concentrated draining sequence. The concentrated buffer draining sequence can be performed in a similar manner for the third through sixth concentrated buffer solutions with the third through sixth buffer inlet ports 203-206, respectively.

Figure 16:
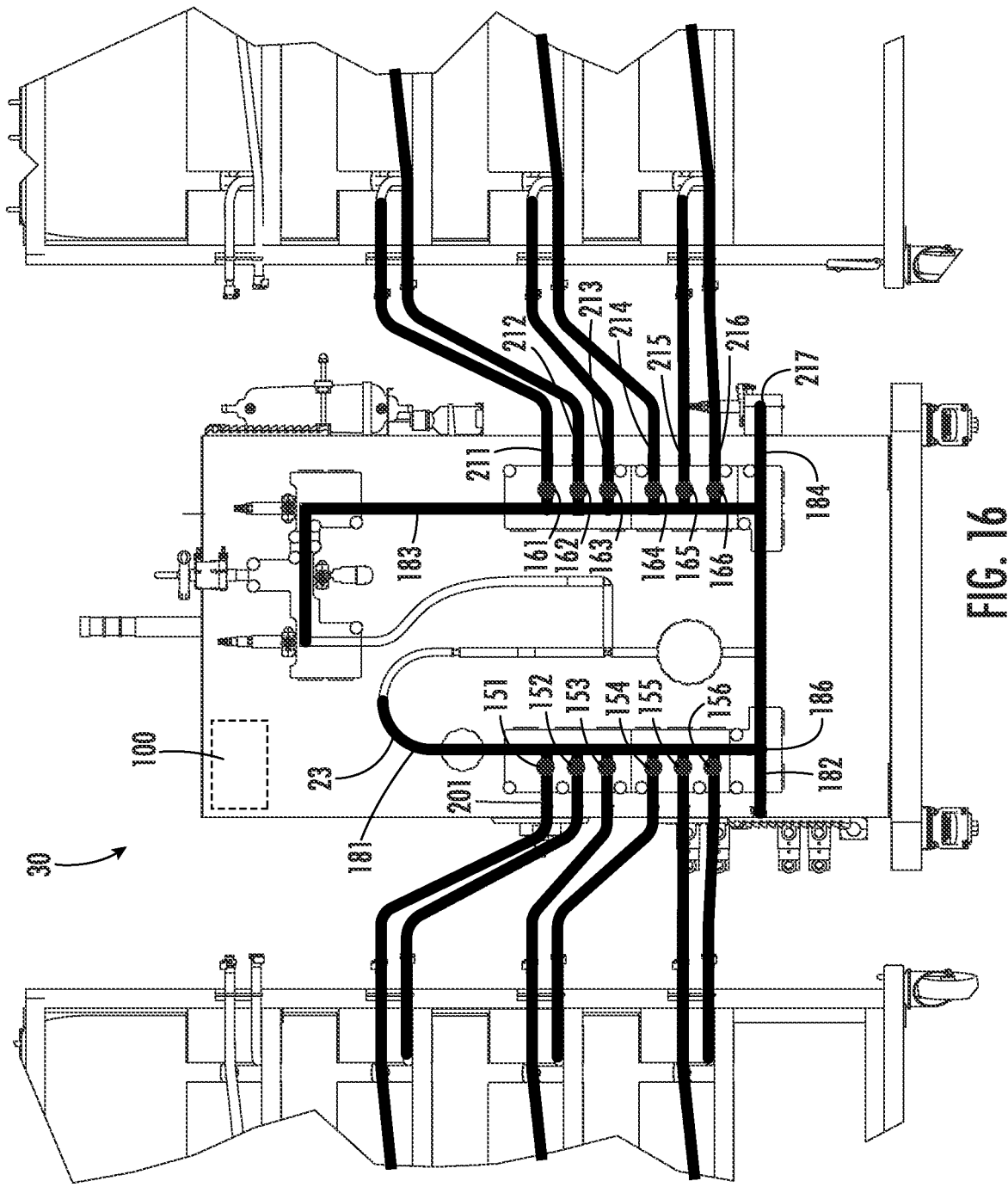
FIG. 16 is a view as in FIG. 8 of the buffer management system, illustrating the manifold in a system draining position.

Referring to FIG. 16, the manifold 23 is in a system draining position. The manifold 23 is maintained in the system draining position so that liquid stored within the system can be drained therefrom.

In the system draining position, the control unit 100 of the dilution skid 30 has controlled the control valves 151-156, 161-166 such that all of the buffer inlet ports 201-206 are in fluid communication with the buffer inlet line 181, and all of the buffer discharge ports 211-16 are in fluid communication with the discharge line 183. The buffer inlet line 181 is in fluid communication with the WFI inlet line 182 via the buffer drain junction 186, which in turn is in fluid communication with the waste line 184. The discharge line 183 is in fluid communication with the waste line 184. In such an arrangement, when the manifold 23 is in the system draining position, there are established multiple flow paths from each buffer inlet ports 201-06 through the manifold 23 to the waste outlet port 217 and from each buffer discharge ports 211-16 through the manifold 23 to the waste outlet port 217. As such, when the manifold 23 is in the system draining position, liquid with the system can drain out the waste outlet port 217 through the effects of gravity. In embodiments, the manifold 23 can be placed in a variety of suitable configurations and taken through a variety of sequences in order to effectively drain fluid from the manifold 23. Those skilled in the art will appreciate that this operation can be accomplished by a variety of techniques of which the skilled artisan will be familiar.

In embodiments, the control unit 100 is configured to place all of the control valves in an open position when the manifold 23 is in the system draining position. The system draining position can be used to help drain liquids from the manifold 23. With all control valves being opened, surplus liquid within the manifold 23 can be allowed to flow to the drain point by the effect of gravity. The air line 190 on the top of the manifold 23 can be opened to help displace the liquid from the manifold 23. Draining fluid within the manifold 23 can help facilitate the handling and disposal of the used manifold 23.

The control unit 100 can be configured to operate a system draining sequence. In embodiments, the control unit 100 can be configured to operate the system draining sequence by placing the manifold 23 in the system draining position for a predetermined period of time. In embodiments, the buffer management system can include a suitable flow meter along the drain path near the waste outlet port 217 that is communicatively arranged with the control unit 100 to receive a flow signal therefrom indicate of the flow of liquid through the flow path. In embodiments, the control unit 100 can be configured to maintain the manifold 23 in the system draining position at least until the flow signal indicates that the flow of liquid along the drain path is below a predetermined threshold.

Figure 17:
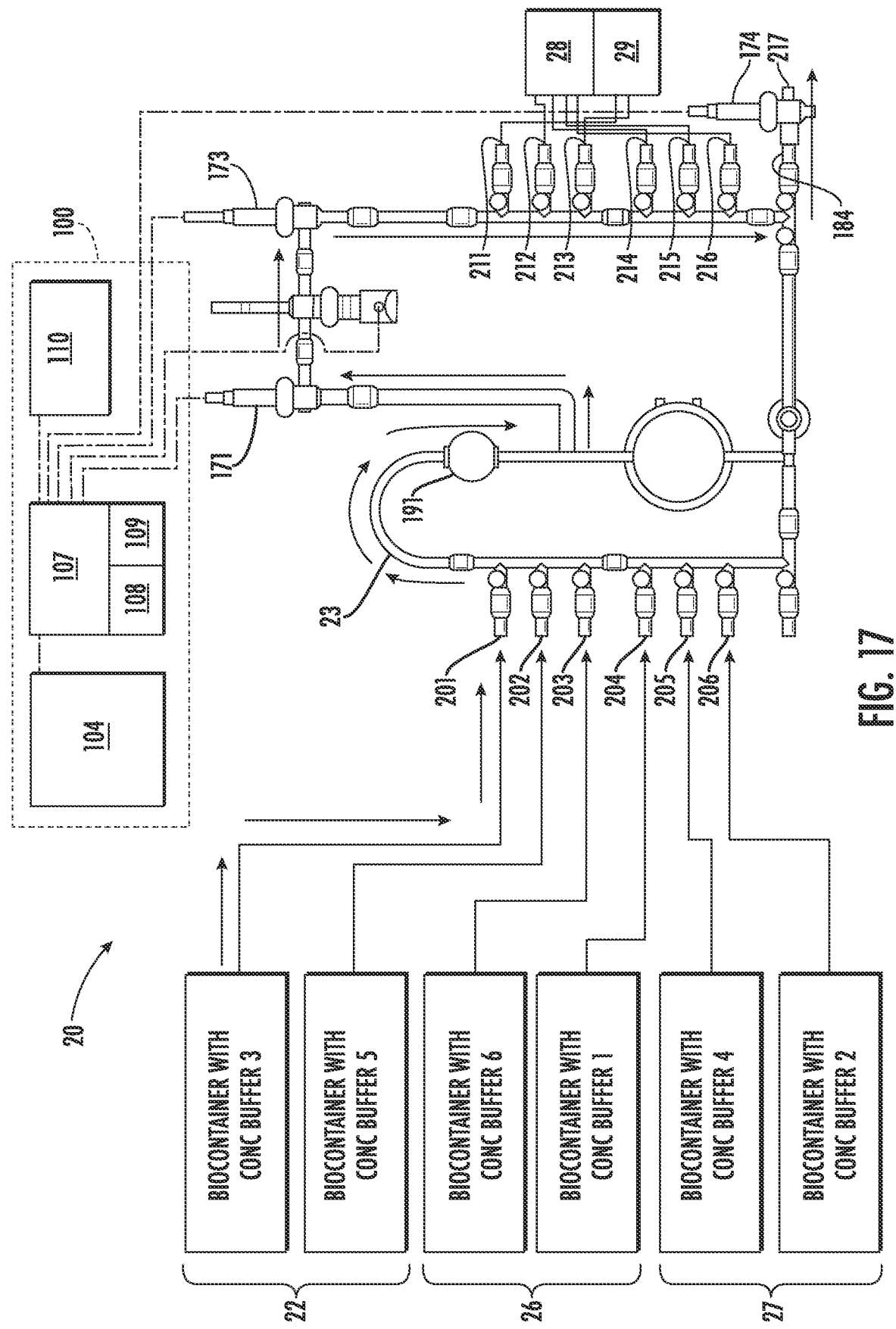
FIG. 17 is a view as in FIG. 14 of the buffer management system, illustrating the manifold in a first concentrated buffer draining position and suitable for use in an embodiment of a process following principles of the present disclosure of identifying an arrangement of different concentrated buffer solutions in fluid communication with a plurality of buffer inlet ports of a manifold of a buffer management system.

Referring to FIG. 17, in embodiments, the buffer management program stored in the computer readable medium 108 of the control unit 100 can include an identification module that is configured to identify automatically buffer solutions passing through the manifold 23. In embodiments, the buffer management program can be configured to identify the flow path of a given buffer solution from the concentrated buffer rack towers 22, 26, 27 through the manifold 23 to the diluted buffer rack towers 27, 28, so the control unit 100 will learn which buffers (concentrated and diluted buffers) respectively pass through which buffer inlet ports 201-06 and buffer outlet ports 211-216 of the manifold 23 of the dilution skid and which biocontainers of the diluted buffer rack towers 27, 28 receives the respective buffer solutions from the manifold 23. With such automatic identification functionality of the buffer management program in place, an operator need not follow a set connection pattern between the totes of the concentrated buffer rack towers 22, 26, 27 and the manifold 23 or the biocontainers of the diluted buffer rack towers 28, 29 and the manifold 23. Once the arrangement of the buffer solutions in the buffer management system 20 is identified, the control unit 100 can transmit this information to the bioprocessing unit 24, so the bioprocessing unit 24 can operate a particular line of the diluted buffer rack towers 28, 29 in order to draw a specific buffer solution thereto.

In embodiments, a user can operate the control unit 100 to input buffer solution characteristic data for each buffer recipe that is selected for use in a given bioprocessing application in which the buffer management system is intended to be used. Table I below contains an example of such buffer characteristic data for a sample of six different buffer solutions, in which the first three buffers are three different concentrated buffers and the last three buffers are their respective equivalents in diluted (lx) form. In embodiments, the buffer characteristic data can include information for each buffer solution concerning suitable characteristics familiar to one skilled in the art, such as, for example, pH, conductivity, and concentration factor. In embodiments, the buffer solution characteristic data can be input to the data storage device 109 of the control unit 100 of the dilution skid 30 via a human machine interface (HMI) 110 of the control unit 100.

In embodiments, the HMI 110 can be located on the dilution skid 30. In other embodiments, the HMI 110 can be part of a mobile application ("app") or otherwise remotely located from the dilution skid 30 and in communication with the control unit 100 via a wireless network. In embodiments, the buffer management program is configured to store the buffer solution characteristic data received through the HMI 110 in a logical manner in the data storage device 109 as part of a recipe manager module of the buffer management program for ready retrieval in processes of identifying buffer solutions following principles of the present disclosure.

TABLE I

Buffer Solution Characteristics

| Buffer | Function | Target pH | Target Conductivity | Concentration Factor |
|---|---|---|---|---|
| 0.2M Sodium Phosphate + 1M NaCl | N/A (concentrate) | 6.44 | 85.7 mS/cm | 20× |
| 1M Glycine-HCl | N/A (concentrate) | 3.06 | 15.9 mS/cm | 10× |
| 0.2M Tris-HCl + 1M NaCl | N/A (concentrate) | 8.14 | 79.6 mS/cm | 20× |
| 10 mM Sodium Phosphate + 50 mM NaCl | Equilibration | 6.99 | 6.29 mS/cm | 1× |
| 0.1M Glycine-HCl | Elution | 3.1 | 2.26 mS/cm | 1× |
| 10 mM Tris-HCl + 50 mM NaCl | Wash 2 | 8.01 | 5.41 mS/cm | 1× |

Referring to FIG. 17, in embodiments of a process following principles of the present disclosure of identifying an arrangement of different buffer solutions in fluid communication with the plurality of buffer inlet ports 201-206 of the manifold 23 of the buffer management system 20, the control unit 100 can be used to place the manifold 23 sequentially in the first through the sixth buffer draining positions to determine which buffer solution is being pulled in by the manifold 23 through the first through the sixth buffer inlet ports 201-06, respectively.

In FIG. 17, a set of concentrated buffer containers 1-6 are connected to the first through sixth buffer inlet ports 201-206 in an uncorrelated manner (i.e., e.g., buffer container 3 is connected to the first buffer inlet port 201 of the manifold 23) that is not known to the buffer management program. The identification module of the buffer management program can be configured to sequentially place the manifold 23 in the first through sixth buffer draining positions to systematically identify which one of the set of concentrated buffers in the concentrated buffer rack towers is connected to which one of the first through sixth buffer inlet ports 201-206.

In embodiments, the buffer management program is configured to go through a sequence of opening the buffer inlet ports 201-206, starting with the first buffer inlet port 201, and opening the first buffer drain path by placing the manifold 23 in the first buffer draining position, as shown in FIG. 17, in which the first buffer inlet port 201 is in fluid communication with the waste outlet port 217. The control unit 100 can operate the buffer pump 191 to draw a supply of the third concentrated buffer from biocontainer 3 the concentrated buffer rack towers 22, 26, 27 (as this is the biocontainer of the concentrated buffer rack towers that is in fluid communication with the first buffer inlet port 201) and convey it through the manifold 23 and out the waste outlet port 217 of the waste line 184.

The first conductivity sensor 171 and the pH sensor 173 can transmit the first conductivity signal and the pH signal to the control unit 100. The identification module of the buffer management program can be configured to analyze at least one of the first conductivity signal and the pH signal to determine which one of the different buffer recipes stored in the data storage device 109 is most closely matched to the buffer solution passing through the manifold 23. In embodiments, the identification module can be configured to use the second conductivity signal from the second conductivity sensor 174 in addition to, or in lieu of, the first conductivity signal and the pH signal. In embodiments, the buffer management program is configured to identify the concentrated buffer passing through the manifold 23 based upon at least one of the values of the conductivity and the pH sensed by the manifold sensors 171, 173, 174 and the buffer recipes stored in the control unit 100, which act as the unique identifier of the buffer. In embodiments, the buffer management program is configured to identify the concentrated buffer passing through the manifold 23 based upon the values of both the conductivity and the pH sensed by the manifold sensors 171, 173, 174 and the buffer recipes stored in the control unit 100, which act as the unique identifier of the buffer. The identification module of the buffer management program is configured to store the identity of the buffer solution fluidly connected to the first buffer inlet port 201 in the data storage device 109 in a logical manner so that this information can be retrieved for later use by the buffer management program.

The above identification steps can be repeated for the remaining second through sixth buffer inlet ports 202-206 by the identification module sequentially placing the manifold 23 in the second through sixth buffer draining positions so that the buffer management program can identify the entire arrangement of all the concentrated buffer solutions and the buffer inlet ports 201-206 of the manifold 23 such that the control unit 100 has identified which concentrated buffer solution is drawn through the manifold 23 when a given one of the buffer inlet ports 201-06 is opened and the buffer pump 191 is operated. The identity of this arrangement can be stored in the data storage device 109 for subsequent use. In embodiments, the buffer management program can be configured to overwrite concentrated buffer connection data stored in the data storage device 109 from prior uses of the buffer management system 20 or to store prior arrangements in a time stamped historical database.

Figure 18:
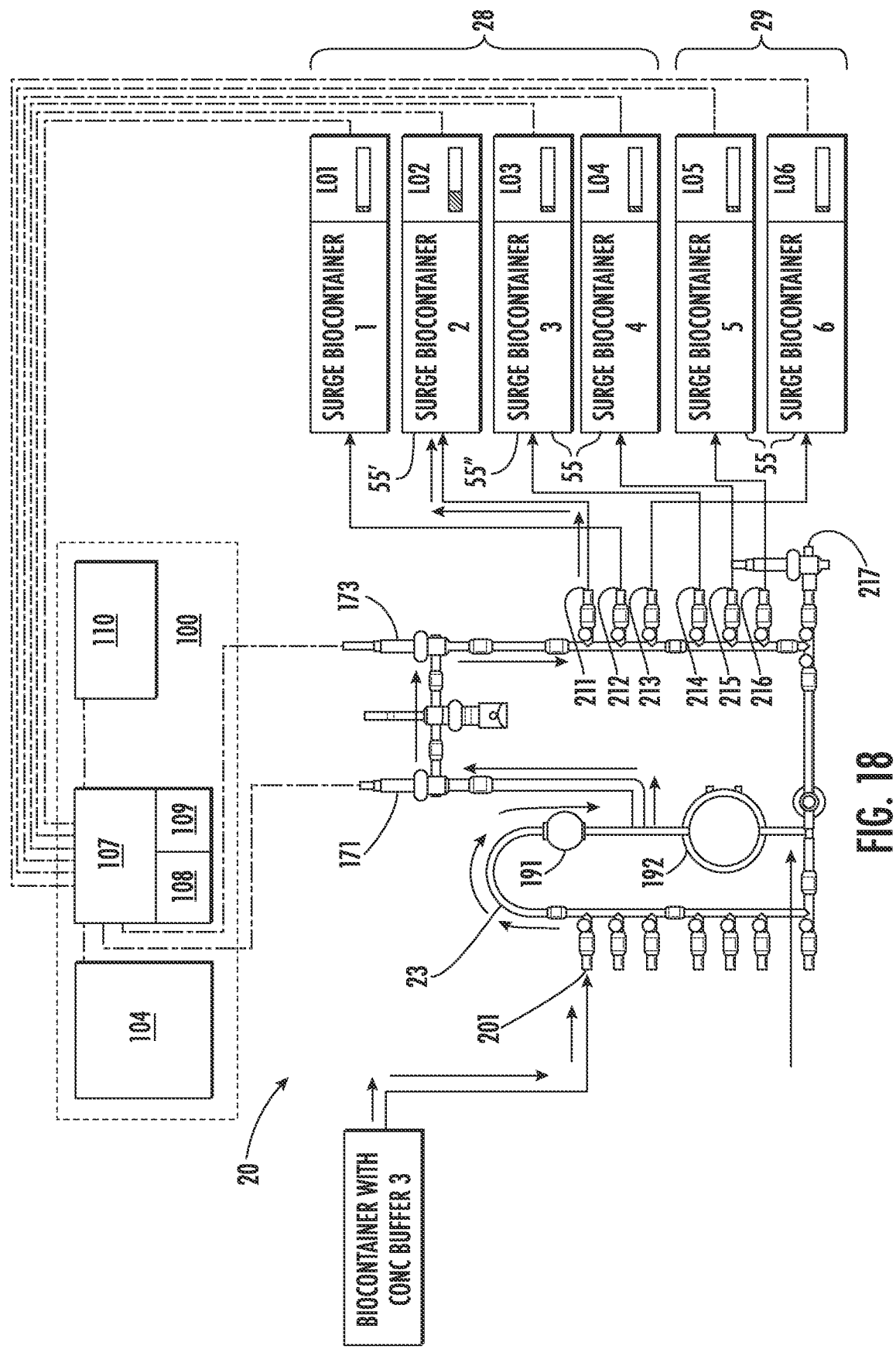
FIG. 18 is a view similar to FIG. 11 of the buffer management system, illustrating the manifold in a first buffer filling position and suitable for use in an embodiment of a process following principles of the present disclosure of identifying an arrangement of biocontainers in fluid communication with a plurality of buffer outlet ports of a manifold of a buffer management system.

Referring to FIG. 18, in embodiments of a process following principles of the present disclosure of identifying an arrangement of different biocontainers 55 in fluid communication with a plurality of the buffer outlet ports 211-216 of the manifold 23 of the buffer management system 23, the control unit 100 can be used to place the manifold 23 sequentially in the first through the sixth buffer filling positions to determine which of the surge biocontainers 55 of the diluted buffer rack towers 28, 29 receives the buffer solution discharged respectively through the first through sixth buffer outlet ports 211-216.

In embodiments, the buffer discharge ports 211-216 of the manifold 23 are in respective fluid communication with a different one of the surge biocontainers 55 of the diluted buffer rack towers 28, 29. In FIG. 18, a set of surge biocontainers 55 of the diluted buffer rack towers 28, 29 are connected to the first through sixth buffer outlet ports 211-216 in an uncorrelated manner (i.e., e.g., the second surge biocontainer 55" is connected to the first buffer outlet port 211 of the manifold 23) that is not known to the buffer management program.

The identification module of the buffer management program is configured to sequentially discharge fluid through each one of the buffer discharge ports 211-216 to identify which one of the biocontainers 55 is connected to which one of the buffer discharge ports 211-216. The identification module of the buffer management program can sequentially place the manifold 23 in the first through sixth buffer filling positions to systematically identify which one of the set of surge containers 55 of the diluted buffer rack towers 28, 29 is connected to which one of the first through sixth buffer outlet ports 211-216.

In embodiments, the identification module of the buffer management program can be configured to identify automatically the biocontainer 55 with which each one of the buffer discharge ports 211-216 is in fluid communication based upon the change of the fill level signal therefrom. In embodiments, a suitable fill level sensor L01-L06 is respectively associated with each one of the surge biocontainers 55. Each of the fill level sensors L01-L06 is in electrical communication with the control unit 100 to transmit the respective fill level signal thereto. Each fill level sensor L01-L06 is configured to configured to detect the amount of material within the surge biocontainer 55 and to generate a fill level signal indicative of the detected amount of material. In embodiments, the fill level sensor L01-L06 can be any suitably type, such as, a capacitive fill level sensor or a load cell, for example. In embodiments, the identification of the particular surge biocontainer 55 receiving the buffer solution from each of the first through sixth buffer inlet ports 211-216 can be determined by monitoring the respective each fill level signal received from each associated fill level sensor L01-L06. The identity of the different fill level sensors L01-L06 (and therefore the different surge biocontainers 55) of the diluted buffer rack towers 28, 29 (e.g. L01 to L06 from top to bottom) is controlled through the control unit 100 of the dilution skid so that the buffer management program is configured to recognize from which fill level sensor L01-L06 a given fill level signal is transmitted.

The identification module of the buffer management program can be configured to identify which one of the surge biocontainers 55 is fluidly connected to the first buffer outlet port 211 and is therefore the particular one of the set of surge biocontainers 55 of the diluted buffer rack towers 28, 29 into which the diluted third buffer solution is stored by monitoring the fill level signals during the first buffer filling position. In embodiments, the identification module can determine which one of the surge biocontainers 55 is fluidly connected to the first buffer outlet port 211 and is therefore the one of the set of surge biocontainers 55 into which the diluted third buffer solution is stored by monitoring for changes in the fill level signal received from the surge containers 55 (i.e., the fill level sensor L01-L06 indicating an increase in the liquid stored within its associated surge biocontainer 55 during the first buffer filling sequence).

In the illustrated embodiment, the identification module is configured to identify the second surge biocontainer 55" as being the one of the set of surge biocontainers 55 in fluid communication with the first buffer outlet port 211 because the second fill level signal from the second surge biocontainer 55", and received by the control unit 100, is changing (increasing) as the diluted third buffer solution is being discharged from the first buffer outlet port 211.

In embodiments, the control unit 100 can be configured to control the operation of the buffer management system such that the fill levels of the other surge containers 55 are not subject to change during this identification process. The identification module of the buffer management program is configured to store the identity of the surge biocontainer 55" fluidly connected to the first buffer outlet port 211 in the data storage device 109 in a logical manner so that this information can be retrieved for later use by the buffer management program.

The above identification steps can be repeated for the remaining second through sixth buffer filling positions so that the buffer management program can identify the entire arrangement of the surge biocontainers 55 of the diluted buffer rack towers 28, 29 and the associated buffer outlet ports 212-216 of the manifold 23 with each being identified and stored in the data storage device 109 for subsequent use. In embodiments, the buffer management program can be configured to overwrite surge biocontainer connection data stored in the data storage device 109 from prior uses of the buffer management system or to store prior arrangements in a time stamped historical database.

In embodiments, the buffer management program goes through a sequence of controlling the control valves to place the manifold 23 in the first buffer stabilizing position as shown in FIG. 10. The control unit 100 operates the buffer pump 191 and the WFI pump 192 so that the third concentrated buffer solution (the buffer management program can retrieve from the data storage device 109 that concentrated buffer 3 is in fluid communication with the first buffer inlet port 201 per the previous identification of concentrated buffers depicted in FIG. 17) and can operate the inline dilution skid such that the third concentrated buffer is in-line diluted with WFI. The fluid mixture is pumped through the in-line conductivity and pH sensors 171, 173 and down to the waste outlet port 217 until the third concentrated buffer solution is diluted to its operational concentration (i.e., lx) and is in specification according to the values detected by the sensors 171, 173.

In embodiments, the buffer management program can be configured to go through a sequence of controlling the control valves to place the manifold 23 in the first buffer filling position as shown in FIG. 18. The buffer pump 191 and the WFI pump 192 continue to draw the third concentrated buffer solution and the WFI through the manifold 23 and out of the first buffer outlet port 211. The buffer management program can be configured to determine that the buffer solution being discharged from the first buffer outlet port 211 is within specification for the third diluted buffer recipe based on the pH/conductivity "fingerprint" sensed by the in-line sensors 171, 173.

Figure 19:
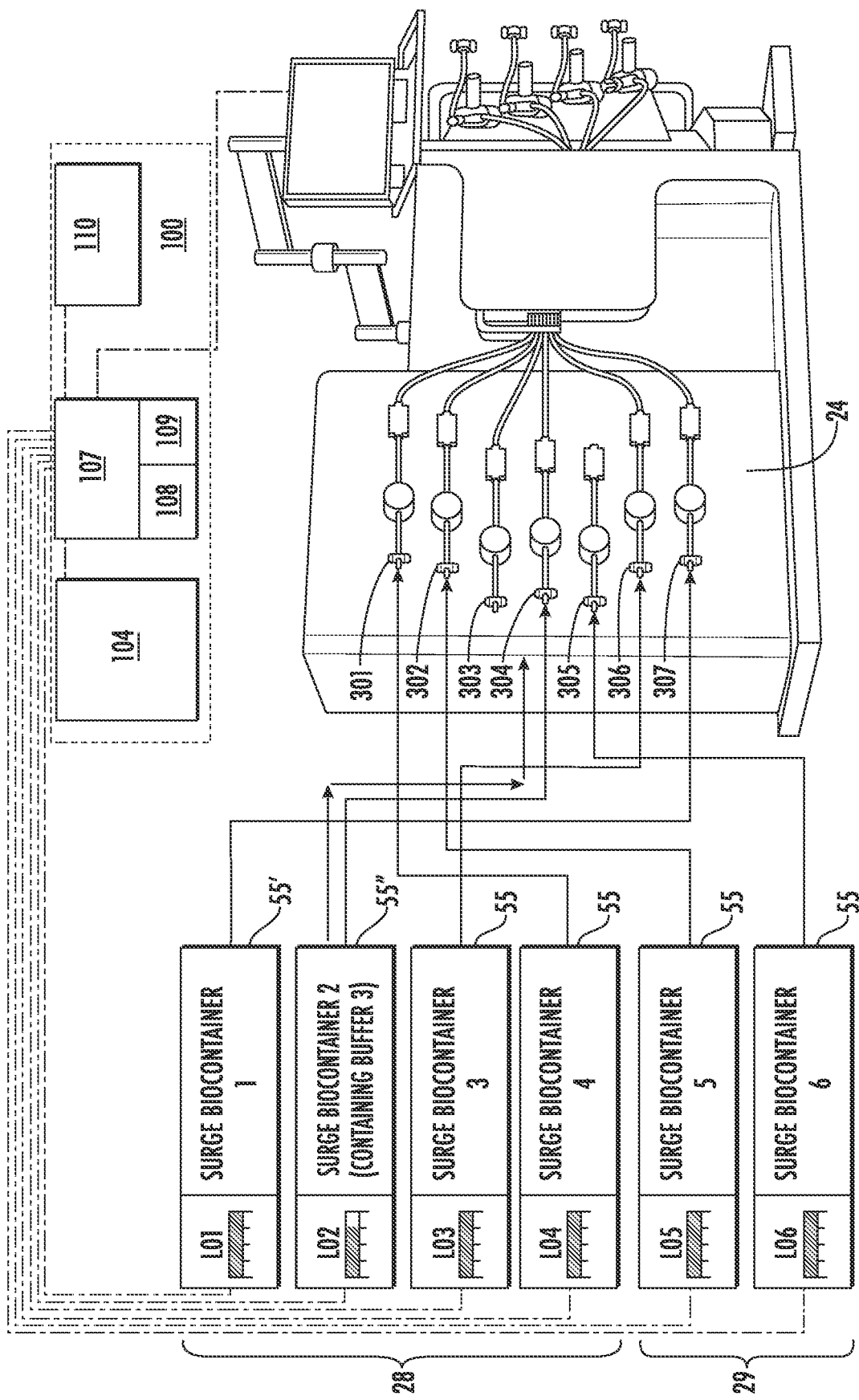
FIG. 19 is a schematic view of the biocontainers of the diluted buffer rack towers and a bioprocessing unit, illustrating an embodiment of a process following principles of the present disclosure of identifying an arrangement of biocontainers in fluid communication with a plurality of inlet ports of a bioprocessing unit.

Referring to FIG. 19, in embodiments, the identification module of the buffer management program is configured to identify automatically which one of the unit inlet ports 301-07 of the bioprocessing unit 24 with which each one of the biocontainers 55 of the diluted buffer rack towers 28, 29 is in fluid communication based upon the change of the fill level signal therefrom. The identification module of the buffer management program is configured to store in the data storage device 109 the identity of which of the unit inlet ports 301-07 of the bioprocessing unit 24 to which each of the biocontainers 55 fluidly connected.

In embodiments of a process following principles of the present disclosure of identifying an arrangement of biocontainers 55 in fluid communication with a plurality of inlet ports 301, 302, 304-307 of the bioprocessing unit 24, the control unit 100 can be used to determine which surge biocontainer 55 of the diluted buffer rack towers 28, 29 discharges buffer solution to the respective unit inlet ports 301, 302, 304-307 of the bioprocessing unit 24. In embodiments, the identification module of the buffer management program can be configured to identify which inlet port 301, 302, 304-07 of the bioprocessing unit 24 receives which buffer solution stored in the diluted buffer rack towers 28, 29.

In FIG. 19, the set of surge biocontainers 55 of the diluted buffer rack towers 28, 29 are connected to six of the unit inlet ports 301, 302, 304-307 of the bioprocessing unit 24 in an uncorrelated manner (i.e., e.g., the second surge biocontainer 55 is connected to the fourth unit inlet port 304 of the bioprocessing unit 24) that is not known to the buffer management program or otherwise available from the data storage device 109.

The identification module of the buffer management program can be configured to identify which one of the surge biocontainers 55" is fluidly connected to the fourth unit inlet port 304 and is therefore the particular one of the set of surge biocontainers 55" of the diluted buffer rack towers 28, 29 from which the diluted third buffer solution will be provided to the bioprocessing unit 24 through the fourth unit inlet port 304 by monitoring the fill level signals. In embodiments, the identification module can determine which one of the surge biocontainers 55" is fluidly connected to the fourth unit inlet port 304 by monitoring for changes in the fill level signal received from the surge containers 55 during a fourth buffer inlet procedure in which the bioprocessing unit 24 is operated to draw buffer solution into it through the fourth unit inlet port 304 (i.e., the fill level sensor L01-L06 indicating a decrease in the liquid stored within its associated surge biocontainer 55 during the fourth buffer inlet procedure).

The identification module of the buffer management program can be configured to sequentially draw in buffer solution from the set of surge biocontainers 55 through an identified one of the unit inlet ports 301, 302, 304-307 of the bioprocessing unit 24 to systematically identify which one of the set of surge containers 55 of the diluted buffer rack towers 28, 29 is fluidly connected to which one of the unit inlet ports 301, 302, 304-307 of the bioprocessing unit 24 based upon a change in the fill level signal received form a particular one of the surge containers 55 of the diluted buffer rack towers 28, 29. The correlation between the second surge biocontainer 55" and the fourth inlet port 304 of the bioprocessing unit 24 can be sent to the control unit 100 of the dilution skid via a communication link established between the two.

In embodiments, the control unit 100 of the dilution skid 30 is in communication with the control system of the bioprocessing unit 24. Upon passage of buffer from the second surge biocontainer 55" to the bioprocessing unit 24, the control unit 100 of the dilution skid 30 detects the liquid level change in the second surge biocontainer 55" and identifies which buffer exactly is transferred to the bioprocessing unit 24 (e.g. Buffer 3, based on FIG. 18 process). This information is passed from the control unit 100 to the control system of the bioprocessing unit 24. At the same time, the control system of the bioprocessing unit 24 identifies which inlet valve is open (e.g. 304) and links the two bits of information together (i.e. Buffer 3 linked to port 304).

In embodiments, the level sensors of the surge bag racks are directly and physically linked to the control system of the bioprocessing unit 24, and this system has locations of level sensors L01-L06 (top to bottom) internally programmed. Then, both the liquid level change and inlet port information are obtained by the control system of the bioprocessing unit 24 directly. In other embodiments, the control unit 100 comprises a centralized supervisory system that is overarching and common to both the dilution skid 30 and the bioprocessing unit 24.

In the illustrated embodiment, the bioprocessing unit 24 comprises a simulated moving bed chromatography unit. In other embodiments, the bioprocessing unit 24 can comprise any suitable unit operation skid that uses multiple buffers for its operation and which can be "buffer inlet agnostic" (i.e., the buffer inlets are not pre-allocated for any specific buffers).

In the illustrated embodiments, the bioprocessing unit 24 is operated so that the fourth inlet port 304 is opened to introduce a buffer solution from the second surge biocontainer bag 55". In embodiments, the bioprocessing unit 24 can communicate to the control unit 100 that the fourth unit inlet port 304 is calling for buffer solution from the diluted buffer rack towers 28, 29. The identification module can be configured to determine which one of the surge biocontainers 55" is fluidly connected to the fourth unit inlet port 304 of the bioprocessing unit 24 by monitoring for changes in the fill level signal received from the fill level sensors L01L-06 associated with the surge containers 55. In the illustrated embodiment, the identification module can identify the second surge biocontainer 55" as being the one of the set of surge biocontainers 55 in fluid communication with the fourth unit inlet port 304 because the fill level signal from the second surge biocontainer 55", and received by the control unit 100, is changing as the third buffer solution is being discharged from the second surge biocontainer 55" to the fourth unit inlet port 304 of the bioprocessing unit 24. In embodiments, the control unit 100 can be configured to control the operation of the buffer management system 20 such that the fill levels of the other surge containers are not subject to change during this identification process. The identification module of the buffer management program can be configured to store the identity of the surge biocontainer 55" fluidly connected to the fourth unit inlet port 304 of the bioprocessing unit 24 in the data storage device 109 in a logical manner so that this information can be retrieved for later use by the buffer management program.

The above identification steps can be repeated for the other unit inlet ports 301, 302, 304-07 of the bioprocessing unit 24 so that the buffer management program can identify the entire arrangement of the surge biocontainers 55 and the associated inlet ports 301, 302, 304-307 of the bioprocessing unit 24 with each such identified arrangement being identified and stored in the data storage device 109 for subsequent use. In embodiments, the buffer management program can be configured to overwrite bioprocessing unit connection data stored in the data storage device 109 from prior uses of the buffer management system 20 or to store prior arrangements in a time stamped historical database.

In embodiments, the identification module can be used for other identification applications. For example, in embodiments, an identification module constructed according to principles of the present disclosure can be used in any system that manages and distributes buffers to another operating system. In embodiments, the inline dilution skid is made for repeated use and is made from suitable materials for that purpose, e.g., made from stainless steel. In embodiments, the biocontainer assemblies of the diluted buffer towers include different types of fill level sensors, such as, for example, load cells or scales.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A buffer management system comprising:
   a set of a concentrated buffer solutions;
   a cabinet;
   a single use manifold, the single use manifold removably mounted to the cabinet and including a plurality of buffer inlet ports and a buffer characteristic sensor in fluid communication with each one of the buffer inlet ports, the plurality of buffer inlet ports in respective fluid communication with a different one of the set of concentrated buffer solutions, the buffer characteristic sensor configured to detect a value of a buffer characteristic of a fluid passing therethrough and to generate a buffer characteristic signal indicative of the sensed value for the buffer characteristic, and
   a control unit, the control unit supported by the cabinet and including a processor, a non-transitory computer readable medium bearing a buffer management program, and a data storage device in operable arrangement with the processor, the processor being in electrical communication with the buffer characteristic sensor to receive the buffer characteristic signal therefrom, the processor programmed with the buffer management program, the buffer management program configured to identify automatically the concentrated buffer solution entering the manifold via one of the buffer inlet ports and passing through the manifold based upon the buffer characteristic signal.

2. The buffer management system according to claim 1, wherein the data storage device includes buffer solution characteristic data for a plurality of buffer recipes, and the buffer management program is configured to identify the concentrated buffer solution passing through the manifold by analyzing the buffer characteristic signal to determine one of the buffer recipes most closely matching the buffer characteristic signal.

3. The buffer management system according to claim 2, wherein the control unit includes a human machine interface (HMI), and wherein the buffer management program is configured to store buffer solution characteristic data for at least one buffer recipe in the data storage device for use by the buffer management program.

4. The buffer management system according to claim 2, wherein the buffer characteristic sensor, the buffer characteristic, and the buffer characteristic signal respectively comprise a first buffer characteristic sensor, a first buffer characteristic, and a first buffer characteristic signal, and wherein the single use manifold includes a second buffer characteristic sensor, the second buffer characteristic sensor configured to detect a value of a second buffer characteristic of the fluid passing therethrough and to generate a second buffer characteristic signal indicative of the sensed value for the second buffer characteristic, the second buffer characteristic being different form the first buffer characteristic, wherein the buffer recipes stored in the data storage device each includes buffer solution characteristic data for the first buffer characteristic and the second buffer characteristic, and wherein the buffer management program is configured to identify the concentrated buffer solution passing through the manifold based upon the values of both the first buffer characteristic signal and the second buffer characteristic sensor.

5. The buffer management system according to claim 4, wherein the first buffer characteristic and the second buffer characteristic respectively comprise conductivity and pH.

6. The buffer management system according to claim 2, wherein the buffer management program is configured to sequentially draw concentrated buffer solution through each one of the buffer inlet ports to identify which one of the set of concentrated buffer solutions is connected to which one of the buffer inlet ports.

7. The buffer management system according to claim 6, wherein the buffer management program is configured to store in the data storage device the identity of the concentrated buffer solution fluidly connected to each one of the buffer inlet ports.

8. The buffer management system according to claim 7, wherein the manifold includes a plurality of buffer discharge ports, the buffer management system further comprising:
   a plurality of biocontainers, the plurality of biocontainers corresponding to the number of the set of concentrated buffer solutions, the plurality of buffer discharge ports in respective fluid communication with a different one of the plurality of biocontainers;
   a plurality of fill level sensors, the plurality of fill level sensors respectively associated with one of the plurality of biocontainers, each fill level sensor configured to configured to detect the amount of material within the biocontainer bag and to generate a fill level signal indicative of the detected amount of material, each of the fill level sensors in electrical communication with the control unit to transmit the respective fill level signal thereto;
   wherein the buffer management program is configured to identify automatically the biocontainer with which each one of the buffer discharge ports is in fluid communication based upon the change of the fill level signal therefrom.

9. The buffer management system according to claim 8, wherein the buffer management program is configured to sequentially discharge fluid through each one of the buffer discharge ports to identify which one of the biocontainers is connected to which one of the buffer discharge ports.

10. The buffer management system according to claim 9, wherein the buffer management program is configured to store in the data storage device the identity of the biocontainer fluidly connected to each one of the buffer discharge ports.

11. The buffer management system according to claim 10, further comprising:
   a bioprocessing unit, the bioprocessing unit including a plurality of unit inlet ports in respective fluid communication with the plurality of biocontainers;
   wherein the buffer management program is configured to identify automatically the unit inlet port with which each one of the biocontainers is in fluid communication based upon the change of the fill level signal therefrom.

12. The buffer management system according to claim 10, wherein the buffer management program is configured to store in the data storage device the identity of the biocontainer fluidly connected to each one of the unit inlet ports of the bioprocessing unit.

* * * * *